United States Patent
Bazinet et al.

(10) Patent No.: US 9,616,083 B2
(45) Date of Patent: *Apr. 11, 2017

(54) OLIGONUCLEOTIDE CHELATE COMPLEX METHODS

(71) Applicant: Replicor Inc., Montreal (CA)

(72) Inventors: Michel Bazinet, Montreal (CA); Andrew Vaillant, Roxboro (CA)

(73) Assignee: REPLICOR INC, Montreal, QC (CA)

( * ) Notice: Subject to any disclaimer, the term of this patent is extended or adjusted under 35 U.S.C. 154(b) by 439 days.

This patent is subject to a terminal disclaimer.

(21) Appl. No.: 13/896,427

(22) Filed: May 17, 2013

(65) Prior Publication Data

US 2013/0310445 A1    Nov. 21, 2013

Related U.S. Application Data

(60) Provisional application No. 61/648,694, filed on May 18, 2012.

(51) Int. Cl.

| | | |
|---|---|---|
| *A61K 31/713* | (2006.01) |
| *A61K 31/7088* | (2006.01) |
| *A61K 31/7115* | (2006.01) |
| *A61K 31/712* | (2006.01) |
| *A61K 31/7125* | (2006.01) |
| *A61K 31/7135* | (2006.01) |

(52) U.S. Cl.
CPC ........ *A61K 31/7088* (2013.01); *A61K 31/712* (2013.01); *A61K 31/713* (2013.01); *A61K 31/7115* (2013.01); *A61K 31/7125* (2013.01); *A61K 31/7135* (2013.01)

(58) Field of Classification Search
CPC .............. A61K 31/7088; A61K 31/713; A61K 31/7125
See application file for complete search history.

(56) References Cited

U.S. PATENT DOCUMENTS

| | | | |
|---|---|---|---|
| 7,358,068 B2 * | 4/2008 | Vaillant et al. ............... 435/91.1 |
| 8,513,211 B2 * | 8/2013 | Vaillant .............. A61K 31/7088 424/1.53 |
| 2002/0166764 A1 | 11/2002 | MacPhee | |
| 2005/0020525 A1 * | 1/2005 | McSwiggen et al. .......... 514/44 |
| 2008/0255030 A1 * | 10/2008 | Yu et al. .......................... 514/3 |

FOREIGN PATENT DOCUMENTS

| | | |
|---|---|---|
| WO | 2007/036016 | 4/2007 |
| WO | 2006/042418 | 4/2008 |
| WO | WO 2009065181 A1 * | 5/2009 |
| WO | 2009/109665 | 9/2009 |
| WO | 2010/107838 A1 | 9/2010 |
| WO | 2012/021985 | 2/2012 |

OTHER PUBLICATIONS

Lee, A.M. et al. Virology:Elsevier. vol. 372. 2008. pp. 107-117.
Vaillant et al., 2006, Antimicrobial Agents and Chemotherapy, 50: 1393-1401.
Bernstein et al., 2008, Antimicrobial Agents and Chemotherapy, 52: 2727-2733.
Lee et al., 2008, Virology, 372: 107-117.
Matsumura et al., 2009, Gastroenterology, 137: 673-681.
Noordeen et al, 2013, Antimicrobial Agents and Chemotherapy, 57: 5291-5298.
Besarab et al., 1981, J Clin Pathol, 34: 1361-1367.
Crooke and Bennett, 1996, Annu Rev Pharmacol Toxicol, 36: 107-129.
Sheehan and Lan, 2016, Blood, 92: 1617-1625.
Marguerie et al., 1979, Biochimica et Biophysica Acta, 579: 134-141.

* cited by examiner

*Primary Examiner* — Jon E Angell

(74) *Attorney, Agent, or Firm* — Norton Rose Fulbright

(57) ABSTRACT

It is described pharmaceutical compositions and methods for the treatment of viral infections, hypercholesterolemia, hypertriglyceridemia, Alzheimer's disease, prion disease and Duchene's muscular dystrophy with oligonucleotide chelate complexes.

28 Claims, 5 Drawing Sheets

```
                        SEQUENCE LISTING

<160> NUMBER OF SEQ ID NOS: 22

<210> SEQ ID NO 1
<211> LENGTH: 40
<212> TYPE: DNA
<213> ORGANISM: Artificial Sequence
<220> FEATURE:
<223> OTHER INFORMATION: REP 2031, fully phosphorothioated

<400> SEQUENCE: 1
cccccccccc cccccccccc cccccccccc cccccccccc                           40

<210> SEQ ID NO 2
<211> LENGTH: 40
<212> TYPE: DNA
<213> ORGANISM: Artificial Sequence
<220> FEATURE:
<223> OTHER INFORMATION: REP 2055, fully phosphorothioated

<400> SEQUENCE: 2
acacacacac acacacacac acacacacac acacacacac                           40

<210> SEQ ID NO 3
<211> LENGTH: 40
<212> TYPE: DNA
<213> ORGANISM: Artificial Sequence
<220> FEATURE:
<223> OTHER INFORMATION: REP 2057, fully phosphorothioated

<400> SEQUENCE: 3
agagagagag agagagagag agagagagag agagagagag                           40

<210> SEQ ID NO 4
<211> LENGTH: 40
<212> TYPE: RNA
<213> ORGANISM: Artificial Sequence
<220> FEATURE:
<223> OTHER INFORMATION: full phosphorothioated, full 2' O methylribose,
      each cytosine 5' methylated

<400> SEQUENCE: 4
cacacacaca cacacacaca cacacacaca cacacacaca                           40
```

```
<210> SEQ ID NO 5
<211> LENGTH: 40
<212> TYPE: DNA
<213> ORGANISM: Artificial Sequence
<220> FEATURE:
<223> OTHER INFORMATION: REP 2056, full phosphorothioated

<400> SEQUENCE: 5
tctctctctc tctctctctc tctctctctc tctctctctc                    40

<210> SEQ ID NO 6
<211> LENGTH: 40
<212> TYPE: DNA
<213> ORGANISM: Artificial Sequence
<220> FEATURE:
<223> OTHER INFORMATION: REP 2133, full phosphorothioated

<400> SEQUENCE: 6
tgtgtgtgtg tgtgtgtgtg tgtgtgtgtg tgtgtgtgtg                    40

<210> SEQ ID NO 7
<211> LENGTH: 16
<212> TYPE: DNA
<213> ORGANISM: Artificial Sequence
<220> FEATURE:
<223> OTHER INFORMATION: miRNA, LNA/DNA, full phosphorothioated
<220> FEATURE:
<221> NAME/KEY: misc_feature
<222> LOCATION: 3, 6, 9, 12, 15
<223> OTHER INFORMATION: LNA
<220> FEATURE:
<221> NAME/KEY: modified_base
<222> LOCATION: 12, 15
<223> OTHER INFORMATION: m5c

<400> SEQUENCE: 7
ccattgtcac actcca                                              16

<210> SEQ ID NO 8
<211> LENGTH: 22
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: 20, 21
<223> OTHER INFORMATION: deoxythymidine
<220> FEATURE:
<221> NAME/KEY: misc_feature
<222> LOCATION: 1-18
<223> OTHER INFORMATION: ribonucleotide

<400> SEQUENCE: 8
ggcuccuuag caaagucaag tt                                       22

<210> SEQ ID NO 9
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: 19, 20
<223> OTHER INFORMATION: deoxythymidine
<220> FEATURE:
<221> NAME/KEY: misc_feature
<222> LOCATION: 1-18
<223> OTHER INFORMATION: ribonucleotide
```

<400> SEQUENCE: 9
cuugacuuug cuaagagcct t                                         21

<210> SEQ ID NO 10
<211> LENGTH: 40
<212> TYPE: DNA
<213> ORGANISM: Artificial Sequence
<220> FEATURE:
<223> OTHER INFORMATION: full phosphorothioate

<400> SEQUENCE: 10
cacacacaca cacacacaca cacacacaca cacacacaca                     40

<210> SEQ ID NO 11
<211> LENGTH: 40
<212> TYPE: DNA
<213> ORGANISM: Artificial Sequence
<220> FEATURE:
<223> OTHER INFORMATION: REP 2148, full phosphorothioate, C = 5'
      methylcytidine

<400> SEQUENCE: 11
acacacacac acacacacac acacacacac acacacacac                     40

<210> SEQ ID NO 12
<211> LENGTH: 40
<212> TYPE: DNA
<213> ORGANISM: Artificial Sequence
<220> FEATURE:
<223> OTHER INFORMATION: full phosphorothioate, C = 5' methylcytidine

<400> SEQUENCE: 12
cacacacaca cacacacaca cacacacaca cacacacaca                     40

<210> SEQ ID NO 13
<211> LENGTH: 40
<212> TYPE: RNA
<213> ORGANISM: Artificial Sequence
<220> FEATURE:
<223> OTHER INFORMATION: full phosphorothioate, full 2' O methyl ribose

<400> SEQUENCE: 13
acacacacac acacacacac acacacacac acacacacac                     40

<210> SEQ ID NO 14
<211> LENGTH: 40
<212> TYPE: RNA
<213> ORGANISM: Artificial Sequence
<220> FEATURE:
<223> OTHER INFORMATION: full phosphorothioate, full 2' O methyl ribose

<400> SEQUENCE: 14
cacacacaca cacacacaca cacacacaca cacacacaca                     40

<210> SEQ ID NO 15
<211> LENGTH: 40
<212> TYPE: DNA
<213> ORGANISM: Artificial Sequence
<220> FEATURE:
<223> OTHER INFORMATION: full phosphorothioate

<400> SEQUENCE: 15
gagagagaga gagagagaga gagagagaga gagagagaga                     40

```
<210> SEQ ID NO 16
<211> LENGTH: 40
<212> TYPE: DNA
<213> ORGANISM: Artificial Sequence
<220> FEATURE:
<223> OTHER INFORMATION: full phosphorothioate

<400> SEQUENCE: 16
ctctctctct ctctctctct ctctctctct ctctctctct                            40

<210> SEQ ID NO 17
<211> LENGTH: 40
<212> TYPE: DNA
<213> ORGANISM: Artificial Sequence
<220> FEATURE:
<223> OTHER INFORMATION: full phosphorothioate

<400> SEQUENCE: 17
gtgtgtgtgt gtgtgtgtgt gtgtgtgtgt gtgtgtgtgt                            40

<210> SEQ ID NO 18
<211> LENGTH: 40
<212> TYPE: RNA
<213> ORGANISM: Artificial Sequence
<220> FEATURE:
<223> OTHER INFORMATION: REP 2139, full phosphorothioate, full 2' O
      methyl ribose, C = 5' methylcytidine

<400> SEQUENCE: 18
acacacacac acacacacac acacacacac acacacacac                            40

<210> SEQ ID NO 19
<211> LENGTH: 20
<212> TYPE: RNA
<213> ORGANISM: Artificial Sequence
<220> FEATURE:
<223> OTHER INFORMATION: antisense, full phosphorothioate, full 2' O
      methyl ribose

<400> SEQUENCE: 19
ucaaggaaga uggcauuucu                                                  20

<210> SEQ ID NO 20
<211> LENGTH: 20
<212> TYPE: DNA
<213> ORGANISM: Artificial Sequence
<220> FEATURE:
<223> OTHER INFORMATION: full phosphorothioate
<220> FEATURE:
<221> NAME/KEY: misc_feature
<222> LOCATION: 1-5, 16-20
<223> OTHER INFORMATION: 2'MOE DNA
<220> FEATURE:
<221> NAME/KEY: modified_base
<222> LOCATION: 12, 15
<223> OTHER INFORMATION: m5c

<400> SEQUENCE: 20
gcctcagtct gcttcgcacc                                                  20

<210> SEQ ID NO 21
<211> LENGTH: 40
<212> TYPE: RNA
<213> ORGANISM: Artificial Sequence
<220> FEATURE:
<223> OTHER INFORMATION: REP 2165, fully phosphorothioated, each
      cytosine 5' methylated
<220> FEATURE:
<221> NAME/KEY: misc_feature
```

```
<222> LOCATION: 1-10, 12-20, 22-30, 32-40
<223> OTHER INFORMATION: 2' O methylribose modification

<400> SEQUENCE: 21
acacacacac acacacacac acacacacac acacacacac                              40

<210> SEQ ID NO 22
<211> LENGTH: 40
<212> TYPE: RNA
<213> ORGANISM: Artificial Sequence
<220> FEATURE:
<223> OTHER INFORMATION: fully phosphorothioated, each cytosine 5'
      methylated
<220> FEATURE:
<221> NAME/KEY: misc_feature
<222> LOCATION: 1-9, 11-19, 21-29, 31-40
<223> OTHER INFORMATION: 2' O methylribose modification

<400> SEQUENCE: 22
cacacacaca cacacacaca cacacacaca cacacacaca                              40
```

OLIGONUCLEOTIDE CHELATE COMPLEX METHODS

CROSS REFERENCE TO RELATED APPLICATION

This application claims priority from U.S. Provisional Application Ser. No. 61/648,694, filed May 18, 2012, the entire content of which is incorporated herein by reference.

TECHNICAL FIELD

The present invention relates to methods for the treatment of diseases involving the administration or use of an oligonucleotide (ON) chelate complex. These diseases can include a viral infection, hypercholesterolemia, hypertriglyceridemia, Alzheimer's disease, prion disease or Duchene's muscular dystrophy.

BACKGROUND ART

ON chelate complexes are two or more ONs linked intermolecularly by a divalent or multivalent metal cation. ON chelate complexes neutralize the inherent chelation properties of ONs which can contribute to administration—related side effects with these compounds. The administration of ON chelate complexes is a novel method of administering an ON to a subject where administration-related side effects associated with un-chelated ONs (which are ONs administered as sodium salts as is commonly used in the art) are mitigated. These side effects may include shivering, fever and chills with intravenous infusion or induration, inflammation and pain at the injection site with subcutaneous administration. Moreover, by preparing ONs as chelated complexes, their pharmacokinetic behaviour may be improved, providing for increased therapeutic performance with similar dosing compared to un-chelated ONs as described in International application publication no. WO 2012/021985 and U.S. application publication no. 2012/0046348, which are incorporated herein by reference in their entirety.

It is thus desirable to be provided with an ON chelate complex acting by a sequence dependent or sequence independent mechanism which will have a therapeutic effect against many disease states including viral infections, hypercholesterolemia, hypertriglyceridemia, Alzheimer's disease or prion disease and which results in the reduction or elimination of administration related side effects common to ONs.

Accordingly, there is a need in the art to be provided with a method for the treatment of the aforementioned disease states which comprises the administration to a subject in need of treatment a pharmaceutical composition comprising an ON chelate complex.

SUMMARY

In accordance with the present description there is now provided a method of treating any disease state which can be affected by treatment with an oligonucleotide by the administration of the oligonucleotide as a chelate complex.

In accordance with the present description there is now provided the use of an oligonucleotide formulated as a chelate complex for treating any disease state which can be affected by treatment with the oligonucleotide.

In accordance with the present description there is now provided the use of an oligonucleotide formulated as a chelate complex in the manufacture of a medicament for treating any disease state which can be affected by treatment with the oligonucleotide.

There is provided a method of treating a viral infection comprising the step of administering an antiviral ON chelate complex to a subject in need of treatment.

There is provided the use of an antiviral ON chelate complex for treating a viral infection.

There is provided the use of an antiviral ON chelate complex in the manufacture of a medicament for treating a viral infection.

In an embodiment, the antiviral oligonucleotide chelate complex comprises at least one oligonucleotide selected from SEQ ID NOs: 1-6 or 10-18.

There is provided a method of treating hypercholesterolemia comprising the step of administering an anti-cholesterol ON chelate complex to a subject in need of treatment.

In an embodiment, the anti-cholesterol oligonucleotide chelate complex comprises at least one oligonucleotide selected from SEQ ID NOs: 1, 2, 3, 5, 6, 10, 11, 12, 15, 16, or 17.

There is provided a method of treating hypertriglyceridemia comprising the step of administering an anti-triglyceride ON chelate complex to a subject in need of treatment.

In an embodiment, the anti-cholesterol oligonucleotide chelate complex comprises at least one oligonucleotide selected from SEQ ID NOs: 1, 2, 3, 5, 6, 10, 11, 12, 15, 16, or 17.

There is provided a method of treating Alzheimer's disease comprising the step of administering an anti-Alzheimer's ON chelate complex to a subject in need of treatment.

There is provided a method of treating prion disease comprising the step of administering an anti-prion ON chelate complex to a subject in need of treatment.

There is provided a method of treating diseases which arise from incorrect splicing during mRNA maturation, which include Duchene's muscular dystrophy (DMD), comprising the step of administering an ON chelate complex designed to correct the incorrect splicing in DMD.

There is provided the use of an antiviral ON chelate complex for treating a viral infection.

There is provided the use of an antiviral ON chelate complex in the manufacture of a medicament for treating a viral In an embodiment, the antiviral oligonucleotide chelate complex comprises at least one oligonucleotide selected from SEQ ID NOs: 1-6 or 10-18.

There is provided the use of an anti-cholesterol ON chelate complex for treating hypercholesterolemia.

There is provided the use of an anti-cholesterol ON chelate complex in the manufacture of a medicament for treating hypercholesterolemia.

In an embodiment, the anti-cholesterol oligonucleotide chelate complex comprises at least one oligonucleotide selected from SEQ ID NOs: 1, 2, 3, 5, 6, 10, 11, 12, 15, 16, or 17.

There is provided the use of an anti-triglyceride ON chelate complex for treating hypertriglyceridemia.

There is provided the use of an anti-triglyceride ON chelate complex in the manufacture of a medicament for treating hypertriglyceridemia.

In an embodiment, the anti-triglyceride oligonucleotide chelate complex comprises at least one oligonucleotide selected from SEQ ID NOs: 1, 2, 3, 5, 6, 10, 11, 12, 15, 16, or 17.

There is provided the use of an anti-Alzheimer's ON chelate complex for treating Alzheimer's disease.

There is provided the use of an anti-Alzheimer's ON chelate complex in the manufacture of a medicament for treating Alzheimer's disease.

There is provided the use of an anti-prion ON chelate complex for treating prion disease.

There is provided the use of an anti-prion ON chelate complex in the manufacture of a medicament for treating prion disease.

There is provided the use of an ON chelate complex designed to correct the incorrect splicing in DMD for treating diseases which arise from incorrect splicing during mRNA maturation, which include Duchene's muscular dystrophy (DMD).

There is provided the use of an ON chelate complex designed to correct the incorrect splicing in DMD in the manufacture of a medicament for treating diseases which arise from incorrect splicing during mRNA maturation, which include Duchene's muscular dystrophy (DMD).

There is provided a method for the treatment of hypercholesterolemia, the method comprising the administration of an oligonucleotide chelate complex comprising SEQ ID NO: 20.

There is provided the use of an oligonucleotide chelate complex comprising SEQ ID NO:20 for the treatment of hypercholesterolemia.

There is provided the use of an oligonucleotide chelate complex comprising SEQ ID NO:20 in the manufacture of a medicament for the treatment of hypercholesterolemia.

There is provided a method for the treatment of Duschene's muscular dystrophy, the method comprising the administration of an oligonucleotide chelate complex comprising SEQ ID NO:19.

There is provided the use of an oligonucleotide chelate complex comprising SEQ ID NO:19 for the treatment of Duschene's muscular dystrophy.

There is provided the use of an oligonucleotide chelate complex comprising SEQ ID NO:19 in the manufacture of a medicament for the treatment of Duschene's muscular dystrophy.

There is provided a method for the treatment of hepatitis C infection, the method comprising the administration of an oligonucleotide chelate complex comprising SEQ ID NO:7.

There is provided the use of an oligonucleotide chelate complex comprising SEQ ID NO:7 for the treatment of hepatitis C infection.

There is provided the use of an oligonucleotide chelate complex comprising SEQ ID NO:7 in the manufacture of a medicament for the treatment of hepatitis C infection.

There is provided a pharmaceutical formulation comprising an antiviral oligonucleotide chelate complex for the treatment of a viral infection.

There is provided a pharmaceutical formulation comprising an anti-cholesterol oligonucleotide chelate complex for the treatment of hypercholesterolemia.

There is provided a pharmaceutical formulation comprising an anti-triglyceride oligonucleotide chelate complex for the treatment of hypertriglyceridemia.

There is provided a pharmaceutical formulation comprising an anti-Alzheimer oligonucleotide chelate complex for the treatment of Alzheimer's disease.

There is provided a pharmaceutical formulation comprising an anti-prion oligonucleotide chelate complex for the treatment of prion disease.

There is provided a pharmaceutical formulation comprising a chelate complex comprising SEQ ID NO:20 for the treatment of hypercholesterolemia.

There is provided a pharmaceutical formulation comprising a chelate complex comprising SEQ ID NO:19 for the treatment of Duchene's muscular dystrophy.

There is provided a pharmaceutical formulation comprising a chelate complex comprising SEQ ID NO:7 for the treatment of hepatitis C infection.

In an embodiment, the oligonucleotide chelate complex is prepared with a divalent metal cation.

In another embodiment, the oligonucleotide chelate complex is prepared with calcium.

In another embodiment, the oligonucleotide chelate complex is prepared with magnesium.

In another embodiment, the oligonucleotide chelate complex is prepared with iron (2+), manganese, copper and/or zinc.

In another embodiment, the oligonucleotide chelate complex comprises two or more different divalent metal cations.

In another embodiment, the oligonucleotide chelate complex comprises calcium and magnesium.

In another embodiment, the oligonucleotide chelate complex comprises at least one double stranded oligonucleotide.

In another embodiment, the oligonucleotide chelate complex comprises at least one oligonucleotide with at least one phosphorothioate linkage.

In another embodiment, the oligonucleotide chelate complex comprises at least one fully phosphorothioated oligonucleotide.

In another embodiment, the oligonucleotide chelate complex comprises at least one oligonucleotide with one 2' modified ribose.

In another further embodiment, the oligonucleotide chelate complex comprises at least one oligonucleotide which has each ribose 2' O-methylated.

In another embodiment, the oligonucleotide chelate complex comprises at least one oligonucleotide which has at least one 5'methylcytosine.

In another embodiment, the oligonucleotide chelate complex comprises at least one oligonucleotide wherein each cytosine is 5'methylcytosine.

In another embodiment, the oligonucleotide chelate complex contains at least one oligonucleotide that is fully phosphorothioated and has all riboses with the 2' O methyl modification and has all cytosines present as 5'methylcytosine.

In another embodiment, the oligonucleotide chelate complex comprises at least one oligonucleotide selected from SEQ ID NOs: 1-6 or 10-18.

In another embodiment, the oligonucleotide chelate complex is formulated for a subcutaneous administration.

In another embodiment, the oligonucleotide chelate complex is formulated for intravenous infusion.

In another embodiment, the oligonucleotide chelate complex is formulated for an administration selected from the group consisting of: intraocular, oral ingestion, enteric, inhalation, intramuscular injection, intraperitoneal injection, intrathecal injection, intrathecal infusion, intratracheal, intravenous injection and topically.

In another embodiment, the oligonucleotide chelate complex is formulated for an administration by aerosol.

In another embodiment, the virus causing the infection is hepatitis B virus.

In another embodiment, the virus causing the infection is a hepadnavirus.

In a further embodiment, the virus causing the infection is hepatitis delta virus.

In another embodiment, the virus causing the infection is influenza.

In another embodiment, the virus causing the infection is selected from the group consisting of: a member of the retroviridae, HIV-1, HIV-2, a member of the herpesviridae, HSV-1, HSV-2, cytomegalovirus, a member of the poxviridae, a member of the paramyxoviridae, respiratory syncytial virus, parainfluenza virus, a member of the bunyaviridae, hantavirus, a member of the filoviridae, Ebola virus, Marburg virus, a member of the flaviviridae, yellow fever virus, dengue virus, West Nile virus, hepatitis C virus, a member of the orthomyxoviridae, a member of the togaviridae, a member of the coronaviridae, a member of the rhabdoviridae, and a member of the arenaviridae.

In another embodiment, the oligonucleotide chelate complex comprises SEQ ID NO:2 (REP 2055).

In another embodiment, the oligonucleotide chelate complex comprises SEQ ID NO:18 (REP 2139).

In another embodiment, the oligonucleotide chelate complex comprises SEQ ID NO:11 (REP 2148).

BRIEF DESCRIPTION OF THE DRAWINGS

Reference will now be made to the accompanying drawings.

DETAILED DESCRIPTION

Figure 2:
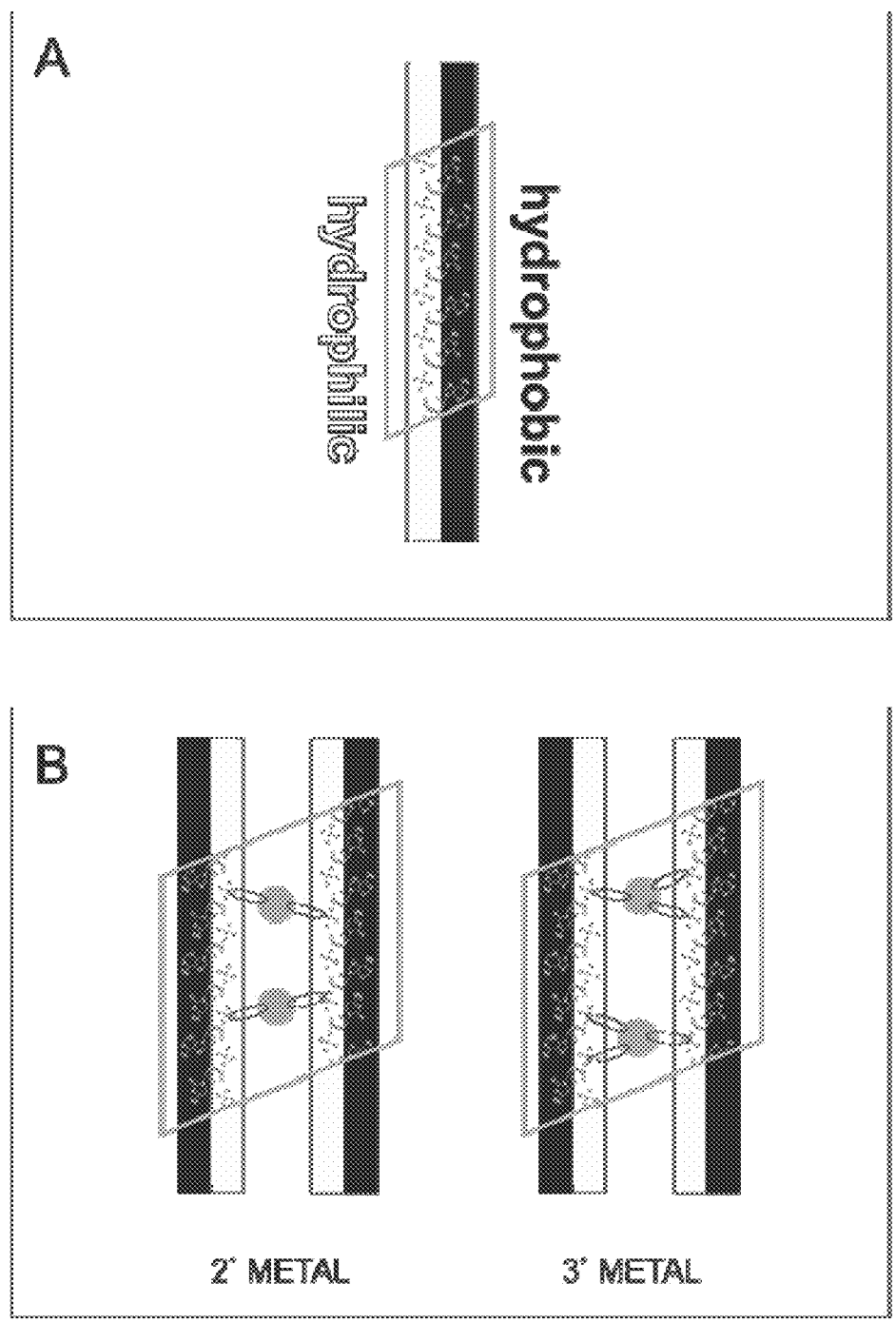
FIG. 2A illustrates the general chemical features of ONs which are not dependent on the ON sequence. Regardless of its sequence, any ON exists as a polymer which has both hydrophobic and hydrophilic activities. Phosphorothioation (depicted in the chemical structure in this figure) serves to increase the hydrophobicity of the ON polymer but does not affect the hydrophilicity.
FIG. 2B conceptualizes the nature of ON chelation of divalent and trivalent metal cations. Metal cations (represented by solid circles) link intermolecularly the hydrophilic surfaces of ON polymers via metal ion bridges (represented by ellipses) between two or three non-bridging oxygen or sulfur atoms in the phosphodiester linkages.

As described in International application publication no. WO 2012/021985 and U.S. application publication no. 2012/0046348, the context of which is incorporated herein by reference in their entirety, ONs in aqueous solutions containing any simple metal cation that is divalent (such as for example but not limited to, $Ca^{2+}$, $Mg^{2+}$ and $Fe^{2+}$) do not exist as salts but rather as chelated complexes of ONs. These complexes are comprised of ON dimers or higher order molecular organizations in which ONs are linked at their phosphodiester backbones via divalent metal ion bridges (see FIG. 2B). At specific ON and metal cation concentrations, these chelated complexes are stable and soluble in aqueous solution and effectively sequester any divalent cations in the ON chelate complexes from solution interaction. This chelate complex formation is also likely to occur with simple metal cations with a 3+ charge or greater (as depicted in FIG. 2B). Thus ONs function as multivalent metal cation chelaters and do not form salts with multivalent metal cations.

ON chelate complexes may contain diverse multivalent metal cations including calcium, magnesium, cobalt, iron, manganese, barium, nickel, copper, zinc, cadmium, mercury and lead. It is further demonstrated that chelation of these multivalent metal cations results in the formation of ON chelate complexes comprised of two or more ONs linked via metal cations and occur with ONs greater than 6 nucleotides in length, and in the presence of ONs with either phosphodiester or phosphorothioate linkages. ONs can optionally have each linkage phosphorothioated. Chelation also occurs with ONs containing 2' modifications (such as 2' O methyl) at the ribose or containing modified bases such as 5'methylcytosine or 4-thiouracil. These 2' modifications can be present on one or more or all riboses and modified bases can be present on one or more bases or be universally present on each base (i.e. all cytosines are present as 5'methylcytosine). Additionally, the ON chelate complexes can comprise ONs which contain multiple modifications such as each linkage phosphorothioated, each ribose 2' modified and each base modified. ON modifications compatible with ON chelate complex formation are further defined below. Moreover, the chelation of the metal cations is not dependent on the sequence of nucleotides present but instead relies on the physiochemical features common to all ONs (see FIG. 2A).

While the formation of ON chelate complexes can be achieved with any divalent metal cation, ON chelate complexes intended for use as medications should preferably contain only calcium and or magnesium but could also contain iron, manganese, copper or zinc in trace amounts and should not include cobalt, barium, nickel, cadmium, mercury, lead or any other divalent metal not listed here.

Importantly, the formation of ON chelate complexes does not occur with monovalent cations such as $Na^+$, $K^+$ or $NH_4^+$ and is thus unlikely to occur with any monovalent cation. Thus, the term "ON salt" is more correctly limited only to ON salts with monovalent cations or with cations which do not form chelate complexes with ONs.

At least a portion of the known transient interaction of ONs with protein components in the blood is likely mediated by the interaction of ONs with metal binding proteins such as albumin and proteins of the calcium-dependent coagulation cascade. Thus the administration of ONs as chelated complexes (which significantly reduce or eliminate their propensity to interact with divalent metal-bound proteins) can mitigate these protein interactions in the blood and result in fewer side effects with ON administration (such as transient anti-coagulation) and may also increase the fraction of ON dose reaching the target organs (e.g. the liver, lungs or spleen) compared to unchelated ONs. Before the present disclosure, the impact of such mitigation on protein interaction on therapeutic activity was unknown and never described.

Fluorescence polarization is a common methodology used to examine intermolecular interactions. In this technique, the bait (i.e. any ON) is labeled with a fluorescent tag (e.g. FITC). In solution, the bait molecule tumbles freely in solution due to Brownian motion which results in poorly polarized fluorescence emission when the bait is subjected to excitation with the correct wavelength of light. With a ligand of sufficient molecular weight (at least the same size as the bait), the interaction between the bait and the ligand introduces a substantial inhibition of the tumbling of the complex in solution. As a result of this inhibited tumbling in solution, fluorescence emission becomes significantly polarized upon excitation. Thus with this technique, interactions can be measured in solution with no physical constraints on either binding partner. Fluorescence polarization is reported as the dimensionless mP, which is directly proportional to the fraction of bound bait molecules in the reaction. For example, if a very small fraction of bait molecules were bound by a particular ligand, there would be very little fluorescence polarization and consequently small mP values. At the other end of the spectrum, if a large proportion of bait molecules were bound by a particular ligand (or with a higher concentration of ligand), there would be substantial fluorescence polarization and consequently large mP values. In this fashion, binding isotherms for particular bait-ligand interactions can be generated by varying concentrations of ligand in the presence of a fixed amount of fluorescently tagged bait.

Herein diverse fluorescently labeled ONs are employed to examine their complex formation in the presence of multivalent metal cations. Although the monitoring of complex formation by fluorescence polarization requires these ONs to be fluorescently labeled, this label is affixed to the ON at the 3' end so as not to interfere with either the nitrogenous base or the phosphodiester backbone of the ON in question. Moreover the fluorescent tag is held away from the ON by a rigid 3 carbon linker to further exclude any perturbation of normal ON behavior in solution. Thus any ON complex formation observed herein using fluorescence polarization with a fluorescently labeled ON is an accurate representation of the solution behavior of unlabeled ONs (whether complexed or not).

The standard in the art clearly teaches the practice of administration of ONs to subjects in need of treatment with ON sodium salts. This is exemplified by the administration of numerous ONs in clinical trials as sodium salts which include Fomivirisen (ISIS 2922), Mipomersen (ISIS 301012), Trecovirsen (GEM 91), Custirsen (OGX-011/ISIS 112989), Genasense (G3139), Aprinocarsem (ISIS 3531/LY 900003), PRO-51 (GSK 2402968) and ALN-RSV01 (Geary et al., 2002, Clin. Pharmacokinetics, 41: 255-260; Yu et al., 2009, Clin. Pharmacokinetics, 48: 39-50; Sereni et al., 1999, J. Clin. Pharmacol., 39: 47-54; Chi et al., 2005, J. Nat. Canc. Inst., 97: 1287-1296; Marshall et al., 2004, Ann. Oncol., 15: 1274-1283; Grossman et al., 2004, Neuro-Oncol, 6: 32-40; Goemans et al., 2011 NEJM 364: 1513-1522). There is no currently published data teaching the formulation of oligonucleotides for any route of parenteral administration with the use of calcium or magnesium or any other divalent metals.

Many of the side effects associated with the administration of sodium salt ONs can be attributable to their chelation effects. The anti-coagulation of blood by ONs is at least in part caused by chelation of serum calcium by ONs thus impairing the calcium dependent coagulation cascade. The chelation of serum calcium and the underlying serum hypocalcemia it can cause is also consistent with the side-effects observed with the administration of ONs by IV administration which includes fever, shivering, weakness and lowering of arterial blood pressure (the latter with rapid IV infusion or injection). Injection site reactions observed with subcutaneous injections of ONs (induration, inflammation, tenderness and pain) is due at least in part to local chelation by ONs of calcium and possibly other divalent cations such as magnesium or multivalent cations at the injection site. The administration of ONs as chelated complexes has been shown to mitigate many of these side effects (see WO 2012/021985).

The term oligonucleotide (ON) refers to an oligomer or polymer of ribonucleic acid (RNA) and/or deoxyribonucleic acid (DNA). This term includes ONs composed of modified nucleobases (including 5'methylcytosine and 4'thiouracil), sugars and covalent internucleoside (backbone) linkages as well as ONs having non-naturally-occurring portions which function similarly. Such modified or substituted ONs may be preferable over native forms because of desirable properties such as, for example, reduced immunoreactivity, enhanced cellular uptake, enhanced affinity for nucleic acid target and increased stability in the presence of nucleases. ONs can also be double stranded.

ONs can include various modifications, e.g., stabilizing modifications, and thus can include at least one modification in the phosphodiester linkage and/or on the sugar, and/or on the base. For example, the ON can include, without restriction, one or more modifications, or be fully modified so as to contain all linkages or sugars or bases with the recited modifications. Modified linkages can include phosphorothioate linkages, phosphorodithioate linkages, and/or methylphosphonate linkages. While modified linkages are useful, the ONs can include phosphodiester linkages. Additional useful modifications include, without restriction, modifications at the 2'-position of the sugar including 2'-O-alkyl modifications such as 2'-O-methyl modifications, 2' O-methoxyethyl (2' MOE), 2'-amino modifications, 2'-halo modifications such as 2'-fluoro; and/or acyclic nucleotide analogs. Other 2' modifications are also known in the art and can be used such as locked nucleic acids. In particular, the ON has modified linkages throughout or has every linkage modified, e.g., phosphorothioate; has a 3'- and/or 5'-cap; includes a terminal 3'-5' linkage; the ON is or includes a concatemer consisting of two or more ON sequences joined by a linker(s). Base modifications can include 5'methylation of the cytosine base (5' methylcytosine or in the context of a nucleotide, 5' methylcytidine) and/or 4'thioation of the uracil base (4'thiouracil or in the context of a nucleotide, 4'thiouridine). Different chemically compatible modified linkages can be combined where the synthesis conditions are chemically compatible such as having an oligonucleotide with phosphorothioate linkages, a 2' ribose modification (such as 2'O-methylation) and a modified base (such as 5'methylcytosine). The ON can further be completely modified with all of these different modifications (e.g. each linkage phosphorothioated, each ribose 2' modified and each base being modified).

In the present description, the term "antiviral ON" refers to any ON which by virtue of its specific biochemical activity (whether sequence dependent or sequence independent) has the ability to directly or indirectly inhibit some aspect of viral replication or to directly or indirectly enhance the host's ability to clear the infection by immunological or other mechanisms.

In the present disclosure, the term "antiviral ON chelate complex" refers to a complex of two or more antiviral ONs in solution linked intermolecularly by a multivalent metal cation. The anti-viral ON chelate complex can contain two or more ONs with different sequences.

In the present disclosure, the term "anti-cholesterol ON" refers to any ON which by virtue of its specific biochemical activity (whether sequence dependent or sequence independent) has the ability to directly or indirectly reduce abnormally elevated total serum cholesterol and or low/very low density lipoprotein serum levels in a subject.

In the present disclosure, the term "anti-cholesterol ON chelate complex" refers to a complex of two or more anti-cholesterol ONs linked intermolecularly by a multivalent metal cation. The anti-cholesterol ON chelate complex can contain two or more ONs with different sequences.

In the present disclosure, the term "anti-triglyceride ON" refers to any ON which by virtue of its specific biochemical activity (whether sequence dependent or sequence independent) has the ability to directly or indirectly reduce abnormally elevated serum triglyceride levels in a subject.

In the present disclosure, the term "anti-triglyceride ON chelate complex" refers to a complex of two or more anti-triglyceride ONs linked intermolecularly by a multivalent metal cation. The anti-triglyceride ON chelate complex can contain two or more ONs with different sequences.

In the present disclosure, the term "anti-Alzheimer's ON" refers to any ON which by virtue of its specific biochemical activity (whether sequence dependent or sequence independent) has the ability to:
  A. directly or indirectly stop, retard or reverse amyloid-β accumulation or expression in the brain;
  B. directly or indirectly stop, retard or reverse Alzheimer's plaque formation or growth in the brain; and/or
  C. directly or indirectly stop, retard or reverse neurological dysfunction associated with the Alzheimer's disease progression.

In the present description, the term "anti-Alzherimer ON chelate complex" refers to a complex of two or more anti-Alzheimer ONs linked intermolecularly by a multivalent metal cation.

In the present description, the term "anti-prion ON" refers to any ON which by virtue of its specific biochemical activity (whether sequence dependent or sequence independent) has the ability to:
  A. directly or indirectly stop, retard or reverse the formation of prion proteins in the periphery or in the brain; and/or
  B. directly or indirectly stop, retard or reverse the neurological dysfunction associated with prion disease.

In the present description, the term "anti-prion ON chelate complex" refers to a complex of two or more anti-prion ONs linked intermolecularly by a multivalent metal cation. The anti-prion ON chelate complex can contain two or more ONs with different sequences.

In the present application, the term "degenerate ON" is intended to mean a single stranded ON having a wobble (N) at every position, such as NNNNNNNNNN. Each base is synthesized as a wobble such that this ON actually exists as a population of different randomly generated sequences of the same length and physiochemical properties. For example, for a degenerate ON 40 bases in length, any particular sequence in the population would theoretically represent only $1/4^{40}$ or $8.3 \times 10^{-25}$ of the total fraction. Given that 1 mole=$6.022 \times 10^{23}$ molecules, and the fact that 1 mole of a 40mer ON would mass approximately 12-14 kg (depending on sequence and modifications present), any ON with a specific sequence present effectively does not exist more than once in any preparation. Thus any chelate formation or biological activity observed in such a preparation must be due to the non-sequence dependent (or independent of the sequence) physiochemical properties of ONs since any particular ON of a defined sequence, being unique in the preparation, cannot be expected to contribute any activity derived from its specific nucleotide sequence.

Figure 1A:
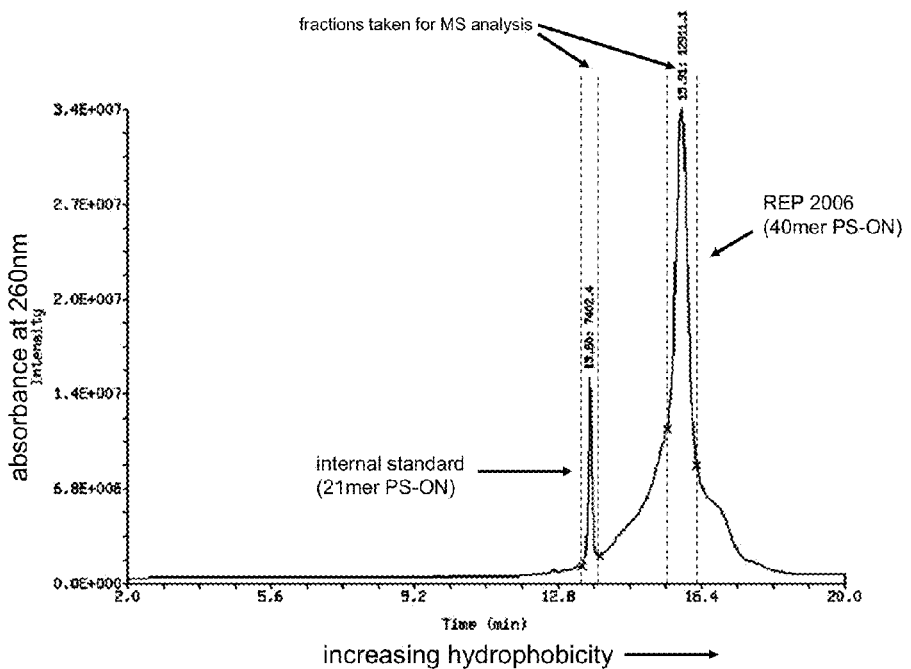
FIG. 1 illustrates the common physiochemical features of ONs. A) Co-separation of REP 2006 and a 21mer phosphorothioate ON with a defined sequence by high performance liquid chromatography. B) Identification of species in the 21mer ON by mass spectroscopy. C) Identification of species in the REP 2006 ON by mass spectroscopy.
Figure 1B:
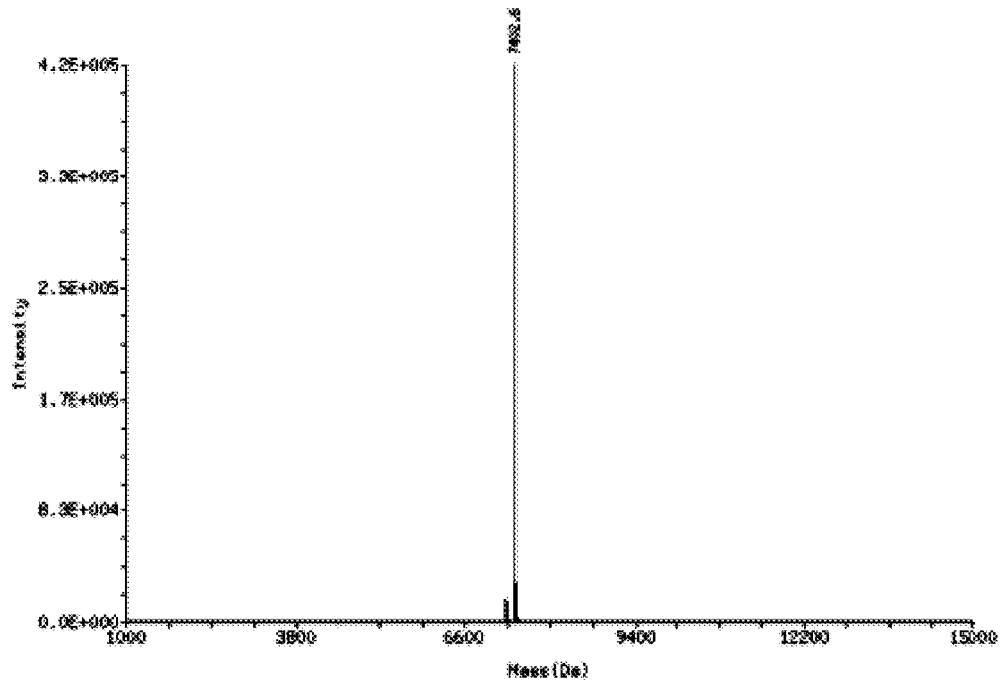
Figure 1C:
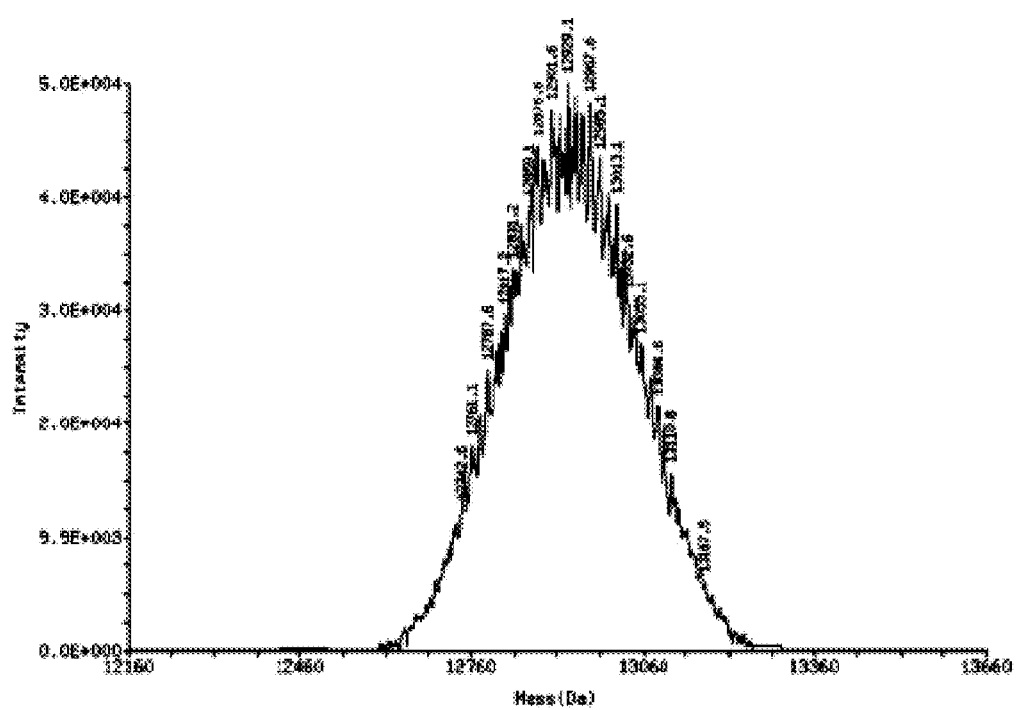

As further illustration of this concept, Example I compares the characterization of REP 2006 (a 40mer ON with a degenerate, completely phosphorothioated sequence) with a 21mer ON of a defined sequence (also completely phosphorothioated) by high pressure liquid chromatography and mass spectrometry and clearly shows that any ON with a similar size and chemical modification (i.e. phosphorothioation) will have highly similar (if not identical) physiochemical features which are not affected by the sequence of nucleotides present (see FIGS. 1A-C).

In the present application, the term "nucleic acid polymer" or NAP is intended to identify any single stranded ON which contains no sequence specific functionality. The biochemical activity of NAPs are not dependent on Toll-like receptor recognition of ONs, hybridization with a target nucleic acid or aptameric interaction requiring a specific secondary tertiary ON structure derived from a specific order of nucleotides present. NAPs can include base and or linkage and or sugar modifications as described above.

ONs can exert their effects by numerous mechanisms which are either sequence dependent or sequence independent. Sequence dependent mechanisms are those which require a specific nucleic acid sequence for their activity and where the activity is reduced by one or more alterations in the nucleotide sequence present. This specific sequence may encompass the entire length of the ON or only a portion of it (a sequence motif). Examples of sequence dependent ONs include:
  1. Antisense ONs (either singled stranded or double stranded (e.g. small interfering RNA (siRNA) or small hairpin RNA (shRNA)) are complimentary to a specific portion of a messenger RNA (mRNA) (i.e. a viral mRNA or host mRNA) involved in a disease state (i.e. viral infection or regulation of cholesterol) and when introduced into a cell, they direct the degradation of these target mRNAs by RNAse H or the RNA-induced silencing complex (RISC).
  2. Stearic blocking ONs are single stranded antisense ONs which are complimentary to a specific portion of a mRNA but which are engineered to not activate RNAse H. The hybridization of these ONs to their target mRNA results in a double stranded structure which provides stearic hindrance to proteins normally acting on the mRNA. Such ONs can be employed to block translation of a particular mRNA or to interfere with the post-transcriptional splicing and maturation of a particular mRNA. Such ONs may be engineered to block the activation of RNAse H (since it is not integral to the mechanism of action of these ONs) by 2' ribose modifications throughout or on every ribose present in the ON (such as 2' O methylation).

3. Aptamers are ONs which adopt a specific three dimensional conformation capable of specific protein interaction (i.e. with a viral protein or host protein) and which do not readily interact with host DNA or RNA. Aptamers can also include spiegelmers, which use L-nucleotides to confer resistance to nuclease degradation to the ON.
4. Immunostimulatory ONs utilize a specific timer nucleic acid motif (XXCGXX) to stimulate the immune response in mammals. The optimal motif varies from species to species but is strictly dependent on a specific sequence conforming to the XXCGXX motif.
5. Micro RNAs (miRNAs) bind to and block the function of naturally occurring miRNAs which are involved in a disease state (i.e. viral replication or cholesterol regulation).

Antisense ONs can be applied to various disease states such as targeting viral activity by catalyzing the degradation of a viral mRNA (e.g. ALN-RSV01; Zamora et al., 2011, Am. J. Respir. Crit. Care Med. 183: 531-538) or targeting the production of LDL and VLDL by catalyzing the degradation of the ApoB100 mRNA (e.g. mipomersen [Kynamro™]; Raal et al., 2010, Lancet 375: 998-1006). Antisense ONs can also be used to correct the mis-splicing of gene transcripts which can produce aberrant proteins, such as the correction of the mis-splicing of the dystrophin gene transcript which occurs in Duchenne's Muscular Dystrophy (e.g. PRO-051, Goemans et al., 2011, NEJM 364: 1513-1522).

miRNAs can be applied to various disease states such as hybridizing with and catalyzing the degradation of naturally occurring miR-122 within the cell, which is involved both in the regulation of LDL and VLDL production as well as the production of hepatitis C (e.g. miravirsen: Janssen et al., Mar. 27 2013 NEJM, epub ahead of print).

The only reported example of sequence independent ONs are phosphorothioated NAPs, which selectively interact with amphipathic protein structures in a size (length) dependent fashion by virtue of their physiochemical properties as amphipathic polymers (see e.g. U.S. Pat. No. 8,008,269).

Any ON, regardless of how it exerts its biological effect in a physiological context will be expected to form divalent cation-mediated interactions upon entry of the oligonucleotide into the blood circulation, which contains some free divalent or trivalent cations, but where the bulk of serum divalent metals are protein bound (e.g. calcium bound to calcium binding proteins such as albumin, thrombin and fibrinogen). Therefore, a significant portion of the divalent metal-mediated oligo interactions are likely to be with proteins instead of with another oligonucleotide (in a chelate complex) in an in vivo setting. Since numerous ONs have been shown to have predictable function when administered in vivo according to their design (whether as single stranded antisense, siRNA, shRNA or miRNA), these calcium mediated protein interactions, while having an impact of the tolerability aspects of ONs (as described in the International application publication no. WO2012/021985 and U.S. application publication no. 2012/0046348) appear to be reversible so as to not impede the organ accumulation of ONs, intracellular transport of ONs and the interaction of these ONs with their nucleic acid targets in vivo. The reversibility of these interactions could have been reasonably predicted to be dependent on these divalent metal-mediated oligo-protein interactions. As the administration of chelate complexes of oligonucleotides will likely interfere with these protein interactions (as described in U.S. application publication no. 2012/0046348), one skilled in the art would reasonably predict that administering ON chelate complexes would change the pharmacokinetic behaviours (and organ accumulation) of ONs, especially phosphorothioated ONs (PS-ONs) which are known to accumulate in the kidney, liver, lung and spleen and which are accepted in the art to be dependent on ON-protein interactions.

Additionally, the preparation of ON chelate complexes as described in U.S. application publication no. 2012/0046348 involves ONs interacting in the absence of any protein and in the presence of concentrations of divalent metal cations at higher concentrations than normally present in the blood circulation and it would be reasonably predicted from the art taught as described in U.S. application publication no. 2012/0046348 that these ON chelate complexes would lose their ability to interact normally with proteins in the blood (all ONs must transition through the blood circulation regardless of their ultimate fate in vivo). Therefore while the administration of an ON chelate complex will prevent or mitigate the chelation behaviour of ONs in vivo and thus mitigate the side effects arising from the chelation effects of the oligo, it was not predictable or evident before the present enabling disclosure if the ON used to prepare an ON chelate complex formulations (which were formed ex vivo and in a non-physiological environment) would retain its specific organ accumulation and functionality when administered as a chelate complex (compared to the activity of the ON when administered to a subject as a sodium salt). As the ON chelate complex was not formed in vivo, it may not be able to dissociate and or be transported intracellularly and or adopt the correct protein and or other biochemical interactions in vivo to exert its function (e.g. annealing to a complimentary DNA or RNA strand or interacting with an amphipathic helix in a protein or forming a sequence specific aptameric interaction with a specific protein). Furthermore, the administration of a pre-formed ON chelate complex could result in reduced accumulation in the required location within the host subject in comparison to the same ON when administered as a simple ON salt. Therefore, it was not obvious prior to the disclosures herein that any particular ON chelate complex would retain the biochemical functionality of its un-chelated ON salt progenitor when introduced into a physiological environment or when administered to a subject.

Moreover, because chelation properties and ability to form chelate complexes with divalent metals in solution is inherent in any ON, the demonstration of retention of biological activity with any specific ON when administered as chelate complex will provide clear evidence and teaching that the biological activity of any ON will be retained when administered as a chelate complex, regardless of its specific mode of action or target disease.

Several antiviral ON-based drugs are currently in development for the treatment of viral infections which include the NAPs REP 9AC (REP 2055 or SEQ ID NO:2, REP 9AC' (REP 2139 or SEQ ID NO:18) and REP 9AC-m (REP 2148 or SEQ ID NO:11) for the treatment of HBV, miravirsen for the treatment of HCV and ALN-RSV01 for the treatment of respiratory syncytial virus (RSV). Each of these ONs has a different mechanism of action: nucleic acid-based polymers block HBV viral entry and also prevent the release of the HBV surface antigen protein (HBsAg) into the blood (a protein which inhibits immune function), miravirsen (a miRNA) blocks the action of the micro RNA mir-122 which is known to play a role in HCV replication and ALN-RSV01 (a sRNA) blocks the synthesis of the RSV capsid protein, preventing the production of RSV virions. All of these ON drugs are very effective in eliciting their intended effects in subjects: REP 9AC/REP 9AC' work well to clear HBsAg from the blood, miravirsen works well to inhibit mir-122 function and ALN-RSV-01 works well to block capsid protein production. However in all cases where these ON based compounds are administered parenterally, they are associated with administration-related side effects such as fever, chills, shivering when administered by intravenous infusion or by pain, inflammation or induration at the injection site when administered by subcutaneous administration.

Several ONs have shown efficacy in human patients in treating hypercholesterolemia and hypertriglyceridemia. These are mipomersen (Kynamro™), a second generation antisense oligonucleotide which targets the synthesis of Apo B100, PCS-GaINAc, a sugar conjugated sRNA which targets PCSK9 and NAPs (see Example V).

NAPs have also been shown to be able to prevent the development of prion disease in vitro and in vivo in animals (Kocisko et al., 2006, Antimicrobial Agents and Chemotherapy 50: 1034-1044).

The use of oligonucleotides to correct aberrant RNA splicing in disease states is also an accepted therapeutic intervention in various disease states (Du and Gatti, 2009, Curr. Op. Mol. Ther., 11: 116-123). In the case of Duchene's muscular dystrophy, the oligonucleotide PRO-051 is designed to bind to the dystrophin RNA during maturation and induce the skipping of exon 51 in the mature mRNA which restores normal dystrophin production in diseased muscle fiber (Goemans et al., 2011, NEJM 364: 1513-1522). However classical administration of PRO-051 is accompanied by injection site reactions which result at least in part due to the chelation mediated properties of ONs as described in U.S. application publication no. 2012/0046348.

It is desirable to prepare any of these ON-based drugs as ON chelates in order to minimize their administration-related side effects, provided that they can retain their biochemical functionality. The present disclosures demonstrate that ONs can be prepared as chelate complexes and still retain their biochemical functionality. The ON chelate complex in the formulation can be derived from any ON with antiviral activity, examples of which are provided in table 1.

TABLE 1

Examples of ONs which can be prepared as chelate complexes.

| ON class | Nucleic acid type | Sequence (5'-3') | Modifications |
|---|---|---|---|
| NAP | DNA | $(AC)_{20}$ (SEQ ID NO: 2) | All linkages PS |
| NAP | DNA | $(CA)_{20}$ (SEQ ID NO: 10) | All linkages PS |
| NAP | DNA | $(A-5'MeC)_{20}$ (SEQ ID NO: 11) | All linkages PS |
| NAP | DNA | $(5'MeC-A)_{20}$ (SEQ ID NO: 12) | All linkages PS |
| NAP | RNA | $(2'OMeA-2'OMeC)_{20}$ (SEQ ID NO: 13) | All linkages PS |
| NAP | RNA | $(2'OMeC-2'OMeA)_{20}$ (SEQ ID NO: 14) | All linkages PS |
| NAP | DNA | $(AG)_{20}$ (SEQ ID NO: 3) | All linkages PS |
| NAP | DNA | $(GA)_{20}$ (SEQ ID NO: 15) | All linkages PS |
| NAP | DNA | $C_{40}$ (SEQ ID NO: 1) | All linkages PS |
| NAP | DNA | $(TC)_{20}$ (SEQ ID NO: 5) | All linkages PS |
| NAP | DNA | $(CT)_{20}$ (SEQ ID NO: 16) | All linkages PS |
| NAP | DNA | $(TG)_{20}$ (SEQ ID NO: 6) | All linkages PS |
| NAP | DNA | $(GT)_{20}$ (SEQ ID NO: 17) | All linkages PS |
| NAP | RNA | $(2'OMe, 5'MeC-2'OeA)_{20}$ (SEQ ID NO: 4) | All linkages PS |
| NAP | RNA | $(2'OMeA-2'OMe, 5'MeC)_{20}$ (SEQ ID NO: 18) | All linkages PS |

TABLE 1-continued

Examples of ONs which can be prepared as chelate complexes.

| ON class | Nucleic acid type | Sequence (5'-3') | Modifications |
|---|---|---|---|
| miRNA | LNA/DNA | CCATTGTCACA$^m$CTC$^m$CA (SEQ ID NO: 7) | All linkages PS LNA in bold ($^m$C = 5'MeC) |
| miRNA | DNA/RNA | Sequence corresponding to a host micro RNA | All linkages PS, may contain LNA or RNA with 2' ribose modification |
| antisense | DNA/RNA | Sequence corresponding to a viral or host mRNA or gene transcript | All linkages PS, may contain a portion of or all RNA with 2' ribose modification |
| siRNA/shRNA | Double stranded RNA/DNA | Sequence corresponding to HBV X protein | May contain RNA with 2' ribose modification, may contain PS |
| siRNA | Double stranded RNA/DNA | GGCUCCUUAGCAAAGUCAAG$_d$T$_d$T (SEQ ID NO: 8) + CUUGACUUUGCUAAGAGCC$_d$T$_d$T (SEQ ID NO: 9) Sequence corresponding to mRNA for RSV N protein mRNA | All RNA except for deoxythymidine ($_d$T), may contain PS |
| siRNA/shRNA | Double stranded RNA/DNA | Sequence corresponding to a viral mRNA | May contain RNA with 2' ribose modification, may contain PS |
| antisense | RNA/DNA | GCCTCAGTCTG$^m$CTT$^m$CGCACC (SEQ ID NO: 20) | All linkages PS 2'MOE RNA in bold ($^m$C = 5'MeC) |
| antisense | RNA or DNA | targeting PKCS9 | All linkages PS, may contain 5'MeC |
| siRNA | Double stranded RNA/DNA | targeting PKCS9 | May contain RNA with 2' ribose modification, may contain PS, may contain GaINAc conjugates |
| antisense | RNA | UCAAGGAAGAUGGCAUUUCU (SEQ ID NO: 19) | All linkages PS, all riboses 2' O methylated |

LNA = locked nucleic acid, PS = phosphorothioate, 2'OMe = 2' O methyl, 2'MOE = 2'methoxyethyl, 5'MeC = 5'methylcytosine Furthermore, the above compositions may include physiologically and/or pharmaceutically acceptable carriers, adjuvants, vehicles and/or excipients. The characteristics of the carrier may depend on the route of administration. The terms "pharmaceutically acceptable carrier, adjuvant, vehicle and/or excipient" refers to a carrier, adjuvant, vehicle or excipient that may be administered to a subject, incorporated into a composition described herein, and which does not destroy the pharmacological activity thereof. Pharmaceutically acceptable carriers, adjuvants, vehicles and excipients that may be used in the pharmaceutical compositions described herein include, but are not limited to, the following: ion exchangers, alumina, aluminum stearate, lecithin, self-emulsifying drug delivery systems ("SEDDS"), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, wool fat, sodium caprate or tetradecylmaltoside (TDM), TDM derivatives or other alkylated saccharides. Cyclodextrins such as α-, β- and γ-cyclodextrin, or chemically modified derivatives such as hydroxyalkylcyclodextrins, including 2- and 3-hydroxypropyl-β-cyclodextrins, or other solubilized derivatives may also be used to enhance delivery of the compositions described herein.

The compositions described herein may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compositions described herein may be administered by any suitable means, for example, orally, such as in the form of liquid suspensions, tablets, capsules, granules or powders; sublingually; buccally; parenterally, such as by subcutaneous, intravenous, intramuscular, intrathecal injection or infusion techniques (e.g., as sterile injectable aqueous or non-aqueous solutions or suspensions); nasally such as by inhalation spray; topically, such as in the form of a cream or ointment; or rectally such as in the form of suppositories or enema; in dosage unit formulations containing non-toxic, pharmaceutically acceptable vehicles or diluents. The present compositions may, for example, be administered in a form suitable for immediate release or extended release. Immediate release or extended release may be achieved by the use of suitable pharmaceutical compositions, or, particularly in the case of extended release, by the use of devices such as subcutaneous implants or osmotic pumps. Thus, the above compositions may be adapted for administration by any one of the following routes: intraocular, oral ingestion, enteric, inhalation, subcutaneous injection, intramuscular injection, intraperitoneal injection, intrathecal injection or infusion, intratracheal, intravenous injection or infusion, or topically Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compositions may also be delivered through the oral cavity by sublingual and/or buccal administration. Molded tablets, compressed tablets or freeze-dried tablets are exemplary forms which may be used. Exemplary compositions include those formulating the present compositions with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

The effective amount of a compound described herein may be determined by one of ordinary skill in the art, and includes exemplary dosage amounts for an adult human of from about 0.1 to 50 mg/kg of body weight of active compound per day, which may be administered in a single dose or in the form of individual divided doses, such as from 1 to 5 times per day or in doses administered at multiple times during a particular week of administration. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion and clearance, drug combination, and severity of the particular condition. Preferred subjects for treatment include animals, most preferably mammalian species such as humans, and domestic animals such as dogs, cats and the like.

The present disclosure will be more readily understood by referring to the following examples.

EXAMPLE I

Formation of ON Chelate Complexes

FIG. 1A details the separation by HPLC (using a hydrophobic column) of two ON preparations which are co-injected into the column at the same time. The first of these is called the internal standard and is a 21mer phosphorothioate ON with a specific defined sequence, the second is REP 2006 (a 40mer degenerate phosphorothioate ON). Both of these species separate into distinct defined peaks based only on their physiochemical properties (i.e. size and hydrophobicity); the sequence of nucleotides present in each of these ONs has no meaningful impact on their physiochemical properties and therefore has no impact on their separation. As such, the internal standard elutes off the column as a tightly defined peak with smaller retention time as compared to REP 2006, only due to the difference in the size of these two ON polymers. Note that the shoulders on either side of the REP 2006 peak are due to failure sequences typical in the production of longer ONs. Despite the heterogeneous sequence nature of REP 2006, it resolves as a similarly well defined peak by HPLC as the 21mer specific sequence which illustrates the common physiochemical properties of all species in the REP 2006 preparation, even though there are a very large number of different sequences present. Subsequent to the HPLC separation of the REP 2006 and 21-mer peaks, these can be subjected to mass spectroscopy (MS) to identify the species present within these defined peaks (FIGS. 1B and 1C).

In FIG. 1B, the 21mer is resolved into a single species with MW of 7402.6 Da, consistent with this PS-ON having a defined sequence. However, MS analysis of REP 2006 (FIG. 1C) reveals an extremely large number of species present whose mass range has an almost perfect normal distribution, consistent with its completely degenerate nature. This mass range goes from $C_{40}$ (the smallest species) to $A_{40}$ (the largest species) and the prevalence of these species are extremely small with the number of species increasing (peak intensity) as their mass approaches the center of the mass range. This is because an increasingly larger number of different sequences will result in a similar mass. The fact that all of the different ON species present in REP 2006 have the same retention time on a hydrophobic column during HPLC separation clearly demonstrates that all ONs of the same size and with the same chemical modifications (i.e. phosphorothioation) will have highly similar (if not identical) physiochemical properties and as such, can be considered functionally similar in any application or property which is not dependent on the sequence of nucleotides present in a particular ON molecule. Thus, any ON chelate complex formation observed with any particular degenerate ON (e.g. REP 2003, REP 2004, see Table 2), cannot be dependent on the sequence of ONs present and must depend on the conserved physiochemical properties of any ON.

The interaction of ON ammonium salts with various divalent metal cations was examined by fluorescence polarization (FP) as described above. During ON synthesis, each ON was conjugated to fluorescein isothiocyanate (FITC) at the 3' end by a rigid 3 carbon linker using well established reagents and synthesis protocols. These ONs were cleaved from the synthesis and left as ammonium salts. The ONs used in this example are described in Table 2.

TABLE 2

Single stranded ONs used in Example I

Figure 3:
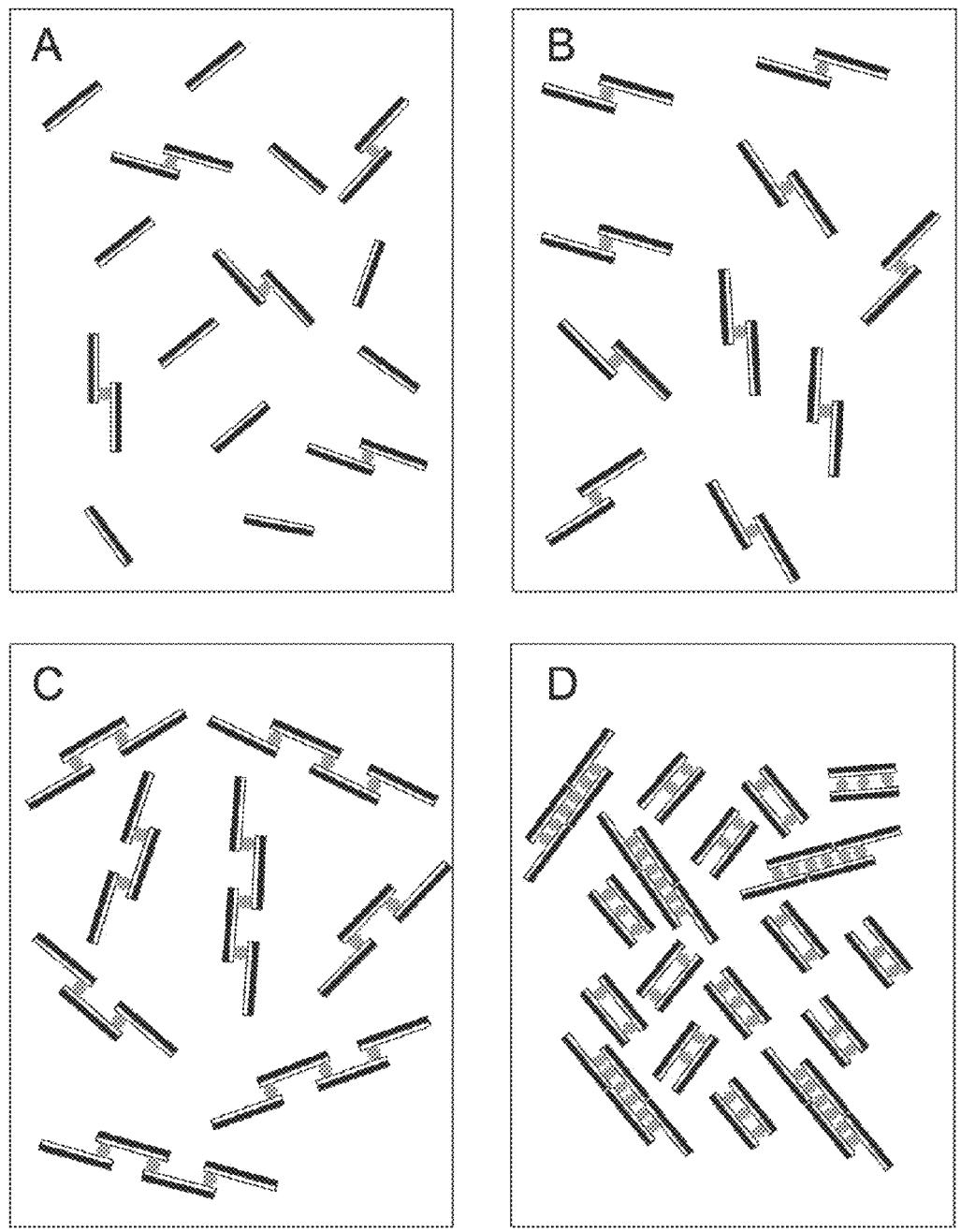
FIG. 3 illustrates the model for solution behaviour of ONs in the presence of divalent or multivalent metal cations at varying ON and divalent metal cation concentrations. A) Low divalent/trivalent metal cation, low ON concentrations yield dimers or low order ON chelate complexes. B) Increasing divalent/trivalent metal cation concentrations yield more complete ON chelate complex formation in the solution. C) Further increasing ON concentrations in the presence of divalent or trivalent metals are capable of yielding higher order ON chelate complexes with increasing metal concentrations. All the chelate complexes in (A) through (C) are soluble in aqueous solution by virtue of having hydrophilic surfaces still exposed to the aqueous environment thus maintaining solubility. D) At sufficient ON and metal concentration, all hydrophilic surfaces are now constrained within the ON chelate complexes, leaving only the hydrophobic surfaces exposed to the aqueous environment. This results in precipitation of the ON chelate complex.
Figure 4:
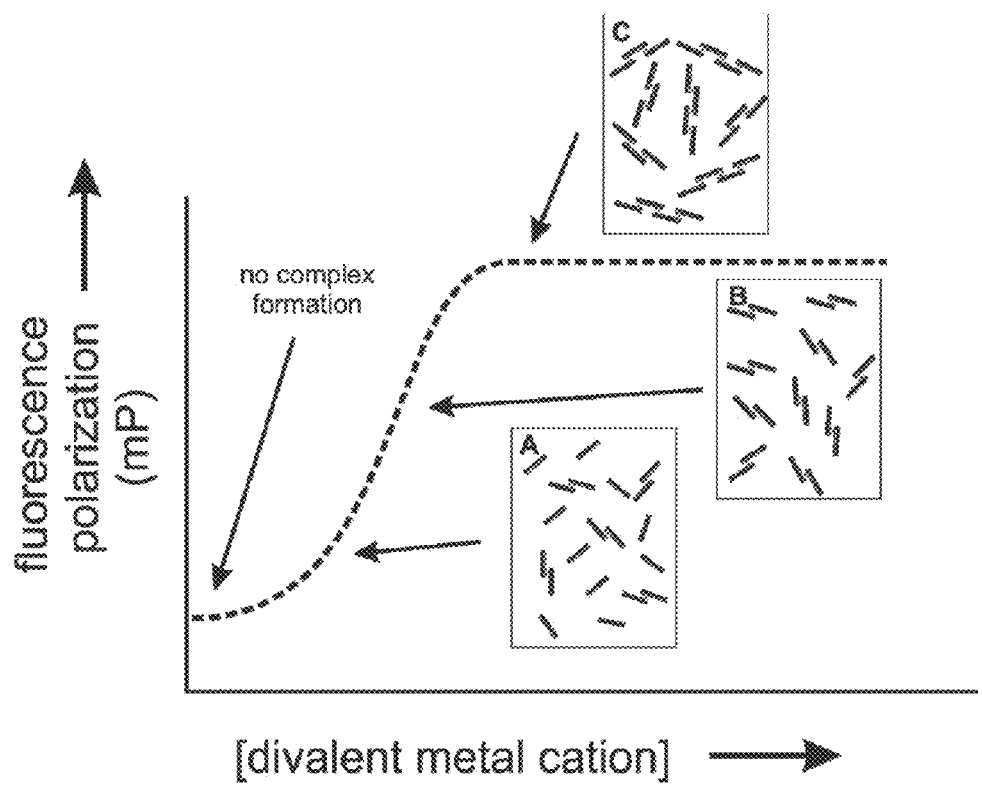
FIG. 4 illustrates the effect of the solution behaviour of fluorescent-ON chelate complexes on fluorescence polarization. With increasing metal concentration, the size (and mass) of ON chelate complex formation also increases (see FIG. 3) and thus tumbles more slowly in solution. This slower tumbling of the complex in solution leads to increased fluorescence polarization and an increased mP value.

| ON | Sequence (5'-3') | Modifications |
|---|---|---|
| REP 2032-FL | $N_6$ | PS (DNA) |
| REP 2003-FL | $N_{10}$ | PS (DNA) |
| REP 2004-FL | $N_{20}$ | PS (DNA) |
| REP 2006-FL | $N_{40}$ | PS (DNA) |
| REP 2107-FL | $N_{40}$ | PS + 2' O Me (RNA) |
| REP 2086-FL | $N_{40}$ | 2' O Me (RNA) |
| REP 2031-FL | $C_{40}$ (SEQ ID NO: 1) | PS (DNA) |
| REP 2055-FL | $(AC)_{20}$ (SEQ ID NO: 2) | PS (DNA) |
| REP 2057-FL | $(AG)_{20}$ (SEQ ID NO: 3) | PS (DNA) | modified and each cytosine 5' methylated; SEQ ID NO:18). Each of these ONs was prepared as a 0.5 mM stock in 1 mM TRIS (pH 7.2). These stock were used to prepare 3 nM fluorescent ON solutions in FP buffer (10 mM TRIS, 80 mM NaCl, 1 mM EDTA, 10 mM β-mercaptoethanol and 0.1% Tween®-20). EDTA was present to remove any divalent metals present in the solution prior to FP measurements. Each of these buffer solutions also contained 80 mM NaCl to assess ON complex formation in the presence of a molar excess of monovalent cations. To each fluorescent ON in solution was added various amounts of ACS grade chloride salts of divalent (2+) metals (as described in Table 3). The formation of dimers or higher order ON chelate complexes was monitored by an increase in fluorescence polarization (quantified by the dimensionless unit "mP") so that increased formation of ON chelate complexes resulted in larger changes in mass (see FIG. 3). The resulting slower tumbling of these ON chelate complexes in solution leads to increased polarization of emitted fluorescence (see FIG. 4). The results of these experiments are presented in Table 3.

TABLE 3

ON chelate formation with diverse ONs and divalent metals
fluorescence polarization (mP)

| | calcium (as $CaCl_2$) | | | | magnesium (as $MgCl_2$) | | | | iron (as $FeCl_2$) | | | |
|---|---|---|---|---|---|---|---|---|---|---|---|---|
| | absent | | present | | absent | | present | | absent | | present | |
| ON | avg | stdev | avg | stdev | avg | stdev | avg | stdev | avg | stdv | avg | stdev |
| REP 2032-FL | 88.0 | 4.2 | 102.5 | 3.5 | 86* | ND* | 103.5 | 3.5 | 92.0 | 7.1 | 184.5 | 31.8 |
| REP 2003-FL | 68.0 | 4.2 | 100.0 | 9.9 | 66.5 | 9.2 | 92.0 | 2.8 | 60.5 | 10.6 | 117.5 | 16.3 |
| REP 2004-FL | 74.5 | 0.7 | 123.0 | 0.0 | 72.5 | 2.1 | 112.5 | 3.5 | 60.5 | 3.5 | 144.0 | 19.8 |
| REP 2006-FL | 92.0 | 4.2 | 182.5 | 4.9 | 97.0 | 2.8 | 175.5 | 0.7 | 81.5 | 12.0 | 123.0 | 7.1 |
| REP 2107-FL | 73.0 | 15.6 | 95.5 | 0.7 | 67.5 | 3.5 | 87.5 | 3.5 | 61.5 | 3.5 | 117.5 | 13.4 |
| REP 2031-FL | 58.5 | 23.3 | 114.5 | 2.1 | 52.5 | 3.5 | 89.5 | 2.1 | 51.0 | 7.1 | 102.0 | 2.8 |
| REP 2086-FL | 77.0 | 28.3 | 119.5 | 2.1 | 70.0 | 12.7 | 114.0 | 2.8 | 59.5 | 4.9 | 87.0 | 7.1 |
| REP 2055-FL | 48 | 5.7 | 172 | 15.6 | 60.0 | 2.8 | 151.0 | 7.8 | ND | ND | ND | ND |
| REP 2057-FL | 59.5 | 1.4 | 152.5 | 6.36 | 61 | 4.24 | 136.5 | 2.83 | ND | ND | ND | ND |
| REP 2139-FL | 48 | 7.1 | 138.5 | 10.6 | 46 | 0.4 | 142.5 | 7.8 | ND | ND | ND | ND |

Average and standard deviation were based on two replicate measurements.
ND = not determined,
*n = 1

TABLE 2-continued

Single stranded ONs used in Example I

| ON | Sequence (5'-3') | Modifications |
|---|---|---|
| REP 2139-FL | (2'OMeA-2'OMe, 5'MeC)$_{20}$ (SEQ ID NO: 18) | PS + 2'OMe (RNA) |

N = degenerate sequence (random incorporation of A, G, C or T)
PS = phosphorothioation at each linkage
2' O Me = 2' O methylation at each ribose The 3' FITC labeled ONs used were REP 2032-FL (a 6 mer phosphorothioated degenerate oligodeoxynucleotide), REP 2003-FL (a 10mer phosphorothioated degenerate DNA ON), REP 2004-FL (a 20mer phosphorothioated degenerate oligodeoxynucleotide), REP 2006-FL (a 40mer phosphorothioated degenerate DNA ON), REP 2031-FL (a 40mer poly cytidine phosphorothioated DNA ON; SEQ ID NO:1), REP 2107-FL (a 40mer phosphorothioated degenerate RNA ON having each ribose modified by 2' O methylation), REP 2086-FL (a 40mer degenerate phosphodiester RNA ON having each ribose modified by 2' O methylation), REP 2055-FL (a phosphorothioated DNA ON with sequence [AC]$_{20}$; SEQ ID NO:2), REP 2057 (a phosphorothioated DNA ON with sequence [AG]$_{20}$; SEQ ID NO:3) and REP 2139-FL (a phosphorothioated RNA ON with sequence [2'OMeA-2'OMe, 5'MeC]$_{20}$ having each ribose 2' O methyl modified and each cytosine 5' methylated; SEQ ID NO:18).

In each case, significant increases in fluorescence polarization were seen with all ONs in the presence of all divalent cations, indicating the formation of ON chelate complexes with divalent metal cations. These results demonstrate the following:

ONs form dimers and higher order complexes in the presence of calcium, and magnesium. These complexes are expected to form with all other divalent metal cations. The formation of these ON complexes involves the interaction of ONs with these divalent metal cations.

The formation of ON complexes cannot be due to hybridization between nitrogenous bases via traditional Watson-Crick interactions due to the degenerate nature of the ONs tested. Additionally, REP 2031 (SEQ ID NO:1), REP 2055 (SEQ ID NO:2), REP 2057 (SEQ ID NO:3) or REP 2139 (SEQ ID NO:18) cannot self-hybridize under the experimental conditions employed.

The formation of ON complexes is stable and soluble in aqueous solution and since these complexes appear to incorporate the divalent metal in question as part of the complex formed, these ON complexes have the effect of chelating the divalent metal in question from the solution in which the ON complex was formed.

Chelation of these metals and formation of the ON chelate complex is not dependent on a particular nucleotide sequence, as evidenced by the chelation observed with degenerate ONs and also occurs with nucleotide modifications including modification of the phosphodiester linkage or the 2' ribose moiety or modification of the base (e.g. 5'methylcytosine).

Chelation of these metals occurs with ONs in this example from 6-40 nucleotides in length which indicates that ON chelates could form with ONs of any length or greater than 40 nucleotides in length.

EXAMPLE II

Formation of ON Chelate Complexes with Double Stranded ONs

Double stranded ONs are formed as described in WO 2012/021985 from two single stranded complementary ONs which in aqueous solution hybridize to each other via Watson-Crick interactions. Since double stranded ONs still have a phosphodiester backbone exposed on the outside of the DNA helix formed, they should be able to form chelate complexes in the presence of divalent cations. In order to test this hypothesis, two different double stranded DNA ONs were prepared by hybridizing REP 2055-FL (40mer poly AC; SEQ ID NO:2) with REP 2033-FL (40mer poly TG; SEQ ID NO:6) and REP 2057-FL (40mer poly AG; SEQ ID NO:3) with REP 2056-FL (40mer poly TC; SEQ ID NO:5). Because ON hybridization results in a duplex, the resulting increase in mass can be detected by an increase in fluorescence polarization relative to the single stranded ONs used to prepare the complex. Single stranded ONs (REP 2055-FL (SEQ ID NO:2), Rep 2033-FL (SEQ ID NO:6), Rep 2057-FL (SEQ ID NO:3) and REP 2056-FL (SEQ ID NO:5)) were each diluted to 20 nM in 1× FP buffer. The hybridization of the two complementary pairs as identified above were also carried out in 1× FP buffer (10 nM of each ON) and hybridization was confirmed by an increase in fluorescence polarization. The double stranded constructs were then exposed to 100 mM $CaCl_2$ or 100 mM $MgCl_2$. ON chelate complex formation was monitored by a further increase in fluorescence polarization (see Table 4). The results of this experiment confirm the successful hybridization of both complimentary pairs of ONs into double stranded ONs as evidenced by the increase in fluorescence polarization. Moreover, the addition of either $CaCl_2$ or $MgCl_2$ to these double stranded ONs resulted in a further increase in fluorescence polarization, indicating that these double stranded ONs could also form chelate complexes in the presence of divalent metal cations. These results also strongly suggest that double stranded ONs can form ON chelate complexes with any divalent cation and would also be expected to have the effect of sequestering the divalent cations from solution.

TABLE 4

Formation of chelate complexes with double stranded ONs
fluorescence polarization (mP)

| No metal present | | | | | | magnesium (as $MgCl_2$) | | calcium (as $CaCl_2$) | |
|---|---|---|---|---|---|---|---|---|---|
| REP 2055-FL (single stranded) | REP 2033-FL (single stranded) | REP 2057-FL (single stranded) | REP 2056-FL (single stranded) | REP 2055-FL + REP 2033-FL (duplex) | REP 2056-FL + REP 2056-FL (duplex) | REP 2055-FL + REP 2033-FL (duplex) | REP 2056-FL + REP 2057-FL (duplex) | REP 2055-FL + REP 2033-FL (duplex) | REP 2056-FL + REP 2057-FL (duplex) |
| avg  stdev | avg  stdev | avg  stdev | avg  stdev | avg  stdev | avg  stdev | avg  stdev | avg  stdev | avg  stdev | avg  stdev |
| 65.0  7.0 | 65.7  5.2 | 78.3  5.2 | 74.3  7.4 | 119.7  8.6 | 124.7  4.5 | 179.0  15.0 | 178.0  5.4 | 167.0  10.4 | 189.0  5.9 |

Average and standard deviation were based on three replicate measurements.

EXAMPLE III

Antiviral Activity of ON Chelate Complexes in Diverse Enveloped Viruses in vitro Experiments were conducted to verify the antiviral activity of ON chelate complexes in three different enveloped viruses from different viral families: herpes simplex-2 (HSV-2) strain MS (family herpesviridae), influenza A (INFA) strain Hong Kong (family orthomyxoviridae) and respiratory syncytial virus (RSV) strain Long (family paramyxoviridae). For each virus, the efficacy of an ON with known antiviral activity was compared with its calcium chelate in vitro by measuring the inhibition of viral cytopathic effect of each virus on its host cells. For HSV-2 and RSV, Vero cells were used and for INFA, MDCK cells were used. For HSV-2 antiviral evaluations, a plaque reduction assay was used and for INFA and RSV, a cytopathic effect (CPE) assay was used.

For the plaque reduction assay, Vero cells were seeded at 75,000 cells/well in 24 well plates using Vero growth medium. The plates were incubated overnight at 37° C. and 5% $CO_2$. The following day, media was aspirated and approximately 100 plaque forming units (pfu) of HSV was added in a volume of 200 µL of assay medium (Vero growth medium containing 2% FBS). The virus was allowed to adsorb onto the cells for 1 hr at 37° C. and 5% $CO_2$. Compounds were prepared by diluting them in assay medium containing 0.5% Methylcellulose. After the incubation period, 1 mL of each drug dilution was added to triplicate wells of a plate (without aspirating the virus inoculum). The plates were incubated for two days to allow for plaque formation. The media was then aspirated from the wells and the cells fixed and stained using 20% Methanol containing Crystal Violet. Plaques were enumerated by microscopic inspection and the data plotted as percent of virus control.

For the CPE assay, virus and cells were mixed in the presence of test compound and incubated for the required assay duration (5 days for HSV-2 and 7 days for INFA and RSV). Each virus was pre-titered such that control wells exhibited 85 to 95% loss of cell viability due to virus replication. Therefore, antiviral effect or cytoprotection was observed when compounds prevented virus replication. Samples were evaluated for antiviral efficacy with triplicate measurements using 12 concentrations prepared by serial dilution in order to determine $IC_{50}$ values and with duplicate measurements to determine cytotoxicity, if detectable. For the purposes of this study, the FBS concentration in each assay was 0.5%. At assay termination, the assay plates were stained with the soluble tetrazolium-based dye MTS (3-(4, 5-dimethylthiazol-2-yl)-5-(3-carboxymethoxyphenyl)-2-(4-sulfophenyl)-2H-tetrazolium) to determine cell viability. MTS is metabolized by the mitochondrial enzymes of metabolically active cells to yield a soluble formazan product, allowing the rapid quantitative analysis of cell viability and compound cytotoxicity. This reagent is a stable, single solution that does not require preparation before use. At termination of the assay, 10-25 uL of MTS reagent was added per well (10% final concentration based on volume) and the microtiter plates were then incubated for 4-6 hours at 37° C., 5% $CO_2$ to assess cell viability. Adhesive plate sealers were used in place of the lids, the sealed plate was inverted several times to mix the soluble formazan product and the plate was read spectrophotometrically at 490/650 nm with a Molecular Devices Vmax or SpectraMax Plus plate reader. Compounds evaluated for antiviral activity included, REP 2055 calcium chelate and REP 2139 calcium chelate (see Table 5). REP 2055 (a 40mer phosphorothioate DNA ON with sequence $[AC]_{20}$; SEQ ID NO:2) and REP 2139 (a 40mer phosphorothioate RNA ON with sequence $[2'OMeA-2'OMe,5'MeC]_{20}$; SED ID NO:18) are NAPs with broad spectrum antiviral activity against enveloped viruses (Bernstein et al., 2008 Antimicrobial Agents Chemother., 52: 2727-2733; Cardin et al., 2009, Virology J. 6: 214; Vaillant et al., 2006, Antimicrobial Agents Chemother., 50: 1393-1401; Guzman et al., 2007, Antiviral Therapy, 12: 1147-1156; Lee et al., Virology, 372: 107-117; Matsumura et al., 2009, Gastroenterology, 137: 673-681 and U.S. Pat. Nos. 8,008,269, 8,008,270 and 8,067,385). The only required NAP modification for antiviral activity is phosphorothioation of each linkage in the ON. Additional modifications including 2' ribose modifications (such as 2' O methylation) and base modifications (such as 5' methylcytosine and/or 4' thiouracil) have negligible effect on the antiviral activity of NAPs but can be used to optimize tolerability in human patients. REP 2055 and REP 2139 were prepared as calcium chelates according to International application publication no. WO 2012/021985 and U.S. application publication no. 2012/0046348 with the ratio of 30 mg $CaCl_2$ for every 100 mg of ON.

In all three viruses examined the antiviral activity of the REP 2055 calcium chelate and REP 2139 calcium chelate were confirmed. This demonstrates that NAP ONs with broad spectrum antiviral activity against HSV-2, RSV and INFA can be prepared as chelated complexes and still exhibit antiviral activity in these viruses. Moreover, since the antiviral activity of these ONs persisted with their administration as ON chelates, the administration of other classes of ONs (antisense, sRNA, miRNA etc) as ON chelates are also likely to have no significant impact on the biological activity of these ONs. This may be due to the fact that the specific protein interactions (in the case of NAPs or aptamers or CpG ONs) or nucleic acid interactions (in the case of antisense, sRNA or miRNAs) are of much greater affinity than the ON/multivalent metal cation interaction occurring in the ON chelate complex. Combined with the improved toxicological properties of ON chelates versus unchelated ON salts, these experiments suggest that antiviral ONs which are chelated may be more desirable antiviral drugs than their unchelated counterparts. Additionally, ON chelates prepared from nucleic acid-based polymers will be expected to have broad spectrum antiviral activity against enveloped viruses in general as disclosed in U.S. Pat. Nos. 8,008,269, 8,008,270 and 8,067,385.

EXAMPLE IV

ON Chelates are Effective Antiviral Agents Against Chronic HBV Infection in Human Patients Patients with pre-existing chronic HBV infection were subjected to once weekly administration of comparable molar doses of REP 2055 prepared as a simple sodium salt solution according to standard in the art as described above and REP 2139 prepared as a calcium chelate complex (prepared with 30 mg of $CaCl_2$ for every 100 mg of REP 2139 according to International application publication no. WO 2012/021985 and U.S. application publication no. 2012/0046348). The antiviral effects of the administration of the sodium salt NAP (REP 2055) with the calcium chelate NAP (REP 2139-Ca), when given in comparable molar doses using comparable dosing regimens were assessed by reductions in the levels of HBV surface antigen protein (HBsAg) in the blood (as measured by the Abbott Architect™ platform). The antiviral effects of REP 2055 and REP 2139-Ca are presented in Table 6.

TABLE 5

Antiviral activity of ON chelate complexes in vitro

| Virus Strain Cell Type Assay | Compound | $IC_{50}$ (uM) |
|---|---|---|
| HSV-2 Strain MS Vero Cells Plaque Assay | REP 2055 calcium chelate | 1.91 |
| | REP 2139 calcium chelate | 0.445 |
| RSV Strain Long Vero Cells CPE Assay | REP 2055 calcium chelate | 2.97 |
| | REP 2139 Calcium chelate | 2.05 |
| Influenza A Strain Hong Kong MCDK Cells CPE Assay | REP 2055 calcium chelate | 7.53 |

TABLE 6

REP 2055 and REP 2139-Ca comparably clear serum HBsAg in patients with chronic HBV infection

| NAP | Responder patient | Pretreatment serum HBsAg (IU/ml*) | Serum HBsAg on treatment (IU/ml*) |
|---|---|---|---|
| REP 2055 | 1 | 934 | 0.25 |
| | 2 | 1885.4 | 0.38 |
| | 3 | 384.1 | 0 |
| | 4 | 126645.07 | 0.03 |
| | 5 | 158180 | 0 |
| | 6 | 36996.00 | 7 |
| | 7 | 4762.5 | 43.7 |
| REP 2139-Ca | 1 | 70050 | 0.19 |
| | 2 | 13400 | 0 |
| | 3 | 3654.3 | 0.34 |
| | 4 | 47689.7 | 180.44 |
| | 5 | 107659.6 | 32.15 |
| | 6 | 58937.87 | 9.91 |
| | 7 | 17988.99 | 29.21 |

TABLE 6-continued

REP 2055 and REP 2139-Ca comparably clear serum HBsAg in patients with chronic HBV infection

| NAP | Responder patient | Pretreatment serum HBsAg (IU/ml*) | Serum HBsAg on treatment (IU/ml*) |
|---|---|---|---|
| | 8 | 125000 | 0.01 |
| | 9 | 1288.56 | 0.02 |

*as determined by the Abbott Architect ™ quantitative test for HBsAg

Both REP 2055 and REP 2139-Ca are equally active in blocking the release of SVPs from HBV-infected cells at comparable molar doses, which is the therapeutically relevant mechanism of action of all NAPs against HBV infection in general. This activity specifically requires intracellular transport of NAPs into hepatocytes to achieve this functionality. REP 2055 and REP 2139-Ca, when given in comparable monotherapy regimens, achieved comparable HBsAg reduction or clearance in HBV infected patients, which demonstrates the comparable antiviral activity of these two different NAPs and that formulation of REP 2139 as a calcium chelate complex has no discernible effect on its organ accumulation, intracellular transport or biochemical activity.

These results demonstrate that ON chelate complexes, while having the ability to improve the tolerability of ONs, likely by blocking some protein interactions, are also able to disassemble in such a fashion so to not affect the organ accumulation of ONs (in the above example in the liver) or intracellular transport (in the above example into hepatocytes) which are essential for the biochemical activity of NAPs in particular and for many ONs in general. The ability of ON chelate complexes to prevent the protein interactions involved in some aspects of ON tolerability (as taught in U.S. application publication no. 2012/0046348) while still resulting in their unaltered organ accumulation, intracellular transport and biochemical activity were not predictable by one skilled in the art from the teachings in U.S. application publication no. 2012/0046348.

These results clearly demonstrate the effectiveness of an ON chelate for the treatment of chronic HBV infection. Other ONs active against HBV or effective against other viral infections in vivo or in human subjects can be prepared as calcium chelates and with the benefit of the disclosures presented herein, can be reliably expected to retain their therapeutic efficacy while having improved tolerability during compound administration or during the entire treatment regimen as a whole. Having disclosed herein the discovery that an ON chelate complex does not alter the effect in human patients of the ON whose therapeutic activity requires retention of specific organ accumulation, intracellular compartmentalization and biochemical interactions also provides clear teaching that any ON which can be formulated as a chelate complex can be used to achieve its designed therapeutic effect, regardless of its mechanism of action, whether antisense, sRNA, miRNA shRNA or NAP and will have the added benefit of reducing administration related side effects as taught in U.S. application publication no. 2012/0046348.

Additionally, because NAPs have been shown to act against HBV by blocking the release of the HBV surface antigen they will also be active against hepatitis D virus, an unrelated virus which is dependent on the HBV surface antigen for its production. As such, NAP chelate complexes will also be expected to be active against hepatitis delta virus infection.

Importantly, the ON chelate complex administered to patients in the above example showed clear improvement in administration related side effects: IV infusion of the REP 2139 calcium chelate could be completed in two hours and was accompanied by mild shivering or chills only in very infrequent cases. In contrast, REP 2055 administered to human patients as a simple sodium salt at a comparable molar dose to REP 2139-Ca, required greater than 10 hours to complete the IV infusion and still was almost always accompanied by moderate fever, chills and shivering. Additionally, it has been possible with the REP 2139 calcium chelate to administer daily subcutaneous injections for five weeks in human patients without injection site reactions while causing declines in serum HBsAg. Using this route of administration without the appearance of injection site reactions would not have been possible with the subcutaneous administration of a simple ON sodium salt.

These observations demonstrate that antiviral ON chelate complexes are a useful method for the administration of antiviral ONs to a subject without loss of antiviral activity while greatly improving administration related side effects.

These observations further demonstrate that any NAP or antisense ON (including classical antisense, sRNA, miRNA or shRNA ONs) can be formulated as an ON chelate complex without interfering with the ONs intended biological effect and further without interfering with the ONs specific biodistribution or intracellular transport.

EXAMPLE V

NAPS Lower Serum Triglycerides and Cholesterol in vivo

To see if NAPs could prevent the onset of hypercholesterolemia and hypertriglyceridemia in hamsters fed a high fructose (HF) diet, REP 2031, a 40mer fully phosphorothioated oligodeoxycytidylic acid (SEQ ID NO: 1) was administered to animals on a HF diet by intraperitoneal injection 3 times a week for 4 weeks. Several parameters relating to hypercholesterolemia and obesity were monitored (see Table 9)

TABLE 9

Effects of REP 2031 in HF fed hamsters

| | Normal chow | High Fructose Diet | |
|---|---|---|---|
| Parameter measured | diet Normal saline | Normal saline | REP 2031 10 mg/kg |
| Cholesterol (mM) | 3.54 ± 0.304 | 4.432 ± 0.341 | 3.82 ± 0.215 |
| Triglycerides (mEq/l) | 2.295 ± 0.045 | 2.379 ± 0.050 | 2.286 ± 0.032 |

These results show that REP 2031 administration resulted in inhibition of increases in triglycerides and cholesterol associated with a HF diet. Thus ONs can have a therapeutic activity in the prevention of hypercholesterolemia.

Human patients with pre-existing hypercholesterolemia and or hypertriglyceridemia were subjected to once weekly administration of REP 2055 prepared as a calcium chelate complex. The effects of REP 2055 administration on total serum cholesterol, LDL and triglycerides were monitored using accepted laboratory procedures and test methodologies. The effects of REP 2055 treatment on serum cholesterol dynamics are shown in Table 10.

TABLE 10

Effect of REP 2055 treatment on hyperlipidemia in human patients

| Patient | Total cholesterol (mg/dL) | | LDL cholesterol (mg/dL) | | triglycerides (mg/dL) | |
|---|---|---|---|---|---|---|
| | Pre | Treat | Pre | Treat | Pre | Treat |
| 1 | 200 | 160 | 95 | 69 | 155 | 83 |
| 2 | 261 | 135 | 190 | 76 | 130 | 69 |
| 3 | 243 | 171 | 163 | 107 | 185 | 117 |
| 4 | 122 | 110 | 40 | 55 | 215 | 104 |
| 5 | 120 | 118 | 61 | 71 | 93 | 40 |

LDL = low density lipoprotein, Pre = pretreatment baseline, Treat = lowest level achieved on REP 2055 treatment In patients with elevated cholesterol and triglycerides (patients 1-3), REP 2055 treatment resulted in reductions in total and LDL cholesterol as well as serum triglycerides. In patients with normal cholesterol but with mild to moderately elevated triglycerides (patients 4 and 5), REP 2055 treatment had no significant effect on total and LDL cholesterol levels but still resulted in a reduction in serum triglycerides. These data show that the NAP REP 2055 has the ability to reduce or normalize total and LDL cholesterol as well as triglycerides.

In the above example, two different NAPs (REP 2031 [SEQ ID NO: 1] and REP 2055 [SEQ ID NO: 2]), each with a different sequence but having the identical physiochemical properties were able to achieve similar effects in vivo in reducing serum cholesterol and triglycerides. These results clearly demonstrate the sequence-independent activity of NAPs in reducing serum cholesterol and triglycerides and show that any of the NAPs described herein are expected to have similar effect as REP 2013 and REP 2055 shown herein.

Because the antiviral activity, anti-triglyceride, anti-cholesterol and anti-prion activities of NAPs are derived from the same sequence independent properties of phosphorothioated oligonucleotides, the current disclosure of retention of the antiviral activity of NAPs when formulated as chelate complexes against a viral infection provides definitive proof that NAPs will also retain their anti-triglyceride, anti-cholesterol and anti-prion activities as well when administered as ON chelate complexes.

What is claimed is:

1. A method for the treatment of a viral infection, said method comprising the administration of an antiviral oligonucleotide chelate complex comprising at least two oligonucleotides linked at their phosphodiester linkages intermoleculalry by a divalent cation to a subject in need of such treatment.

2. The method of claim 1, wherein said oligonucleotide chelate complex is prepared with calcium.

3. The method of claim 1, wherein said oligonucleotide chelate complex is prepared with magnesium.

4. The method of claim 1, wherein said oligonucleotide chelate complex is prepared with, iron (2+), manganese, copper or zinc.

5. The method of claim 1, wherein said oligonucleotide chelate complex comprises two or more different divalent metal cations.

6. The method of claim 1, wherein said oligonucleotide chelate complex comprises calcium and magnesium.

7. The method of claim 1, wherein said oligonucleotide chelate complex comprises at least one double stranded oligonucleotide.

8. The method of claim 1, wherein said oligonucleotide chelate complex comprises at least one oligonucleotide with at least one phosphorothioate linkage.

9. The method of claim 1, wherein said oligonucleotide chelate complex comprises at least one fully phosphorothioated oligonucleotide.

10. The method of claim 1, wherein said oligonucleotide chelate complex comprises at least one oligonucleotide with one 2' modified ribose.

11. The method of claim 1, wherein said oligonucleotide chelate complex comprises at least one oligonucleotide which has each ribose 2' O-methylated.

12. The method of claim 1, wherein said oligonucleotide chelate complex comprises at least one oligonucleotide which has at least one 5'methylcytosine.

13. The method of claim 1, wherein said oligonucleotide chelate complex comprises at least one oligonucleotide wherein all cytosines are 5'methylcytosine.

14. The method of claim 1, wherein said oligonucleotide chelate complex comprises at least one oligonucleotide that is fully phosphorothioated and has all riboses with the 2' O methyl modification and has all cytosines present as 5'methylcytosine.

15. The method claim 1, wherein said oligonucleotide chelate complex comprises an oligonucleotide selected from SEQ ID NOs: 1-6 or 10-18 and 21-22.

16. The method of claim 1, wherein said oligonucleotide chelate complex is formulated for a subcutaneous administration.

17. The method of claim 1, wherein said oligonucleotide chelate complex is formulated for intravenous infusion.

18. The method of claim 1, wherein said ON chelate complex is formulated for an administration selected from the group consisting of: intraocular, oral ingestion, enteric, inhalation, intramuscular injection, intraperitoneal injection, intrathecal injection, intrathecal infusion, intratracheal, intravenous injection and topically.

19. The method of claim 1, wherein said oligonucleotide chelate complex is formulated for an administration by aerosol.

20. The method of claim 1, wherein the virus causing the infection is hepatitis B virus.

21. The method of claim 1, wherein the virus causing the infection is a hepadnavirus.

22. The method of claim 1, wherein the virus causing the infection is a hepatitis delta virus.

23. The method of claim 1, wherein the virus causing the infection is influenza.

24. The method of claim 1, wherein the virus causing the infection is selected from the group consisting of: a member of the retroviridae, HIV-1, HIV-2, a member of the herpesviridae, HSV-1, HSV-2, cytomegalovirus, a member of the poxviridae, a member of the paramyxoviridae, respiratory syncytial virus, parainfluenza virus, a member of the bunyaviridae, hantavirus, a member of the filoviridae, Ebola virus, Marburg virus, a member of the flaviviridae, yellow fever virus, dengue virus, West Nile virus, hepatitis C virus, a member of the orthomyxoviridae, a member of the togaviridae, a member of the coronaviridae, a member of the rhabdoviridae, and a member of the arenaviridae.

25. The method of claim 1, wherein said oligonucleotide chelate complex comprises an oligonucleotide consisting of SEQ ID NO:2.

26. The method of claim 1, wherein said oligonucleotide chelate complex comprises an oligonucleotide consisting of SEQ ID NO:18.

27. The method of claim 1, wherein said oligonucleotide chelate complex comprises an oligonucleotide consisting of SEQ ID NO:11.

28. The method of claim 1, wherein said oligonucleotide chelate complex comprises an oligonucleotide consisting of SEQ ID NO:21.

* * * * *